United States Patent
Kageyama et al.

(10) Patent No.: US 7,202,032 B2
(45) Date of Patent: Apr. 10, 2007

(54) METHOD OF DETECTING NORWALK-LIKE VIRUS (GI)

(75) Inventors: Tsutomu Kageyama, Saitama (JP); Shigeyuki Kojima, Saitama (JP); Shuetsu Fukushi, Saitama (JP); Fuminori Hoshino, Saitama (JP); Kazuhiko Katayama, Saitama (JP)

(73) Assignee: BML, Inc., Tokyo (JP)

( * ) Notice: Subject to any disclaimer, the term of this patent is extended or adjusted under 35 U.S.C. 154(b) by 255 days.

(21) Appl. No.: 10/381,815

(22) PCT Filed: Mar. 28, 2001

(86) PCT No.: PCT/JP01/02541

§ 371 (c)(1),
(2), (4) Date: Sep. 25, 2003

(87) PCT Pub. No.: WO02/29119

PCT Pub. Date: Apr. 11, 2002

(65) Prior Publication Data

US 2004/0115617 A1    Jun. 17, 2004

(30) Foreign Application Priority Data

Sep. 29, 2000  (JP) .............................. 2000-300723

(51) Int. Cl.
*C12Q 1/68*    (2006.01)
*C07N 21/00*   (2006.01)

(52) U.S. Cl. ........................................ 435/6; 530/24.32

(58) Field of Classification Search .................... 435/5, 435/6; 536/24.3, 24.32, 24.33; 424/204.1
See application file for complete search history.

(56) References Cited

U.S. PATENT DOCUMENTS 5,503,978 A * 4/1996 Schneider et al. .............. 435/6
6,812,339 B1 * 11/2004 Venter et al. ............. 536/24.31

FOREIGN PATENT DOCUMENTS

WO    WO 94/05700    3/1994

OTHER PUBLICATIONS

Vinje et al. Arch Virol. 2000, vol. 145, pp. 223-241.*
Ando et al. J. Clin. Micro. 1995, vol. 33, No. 1, pp. 64-71.*
Wang et al. J. Virol. 1994, vol. 68, No. 9, pp. 5982-5990.*
Sequence search of page 11.*
E.T. Utagawa et al.; "3' Terminal sequence of a small round structured virus (SRSV) in Japan"; Archives of Virology, New York, NY, US, vol. 135, No. 1/2, 1994, pp. 185-192, XP009007985.

* cited by examiner

*Primary Examiner*—Bruce Campell
*Assistant Examiner*—Bao Qun Li
(74) *Attorney, Agent, or Firm*—Sughrue Mion, PLLC

(57) ABSTRACT

A method of detecting a virus in a specimen, whereby a Norwalk-like virus (GI) is detected by using as an index the nucleic acids of a complementary nucleotide sequence corresponding to the 5201- to 5700-positions of the nucleotide sequence of the cDNA of the prototype (standard strain) of the Norwalk-like virus (GI); and a detection kit for performing this method.

20 Claims, 5 Drawing Sheets

SEQUENCE LISTING

<160> NUMBER OF SEQ ID NOS: 57

<210> SEQ ID NO 1
<211> LENGTH: 18
<212> TYPE: DNA
<213> ORGANISM: Norwalk-like Virus (GI)

<400> SEQUENCE: 1
atcgcratct yctgcccg                                                     18

<210> SEQ ID NO 2
<211> LENGTH: 18
<212> TYPE: DNA
<213> ORGANISM: Norwalk-like Virus (GI)

<400> SEQUENCE: 2
accgcratct yttgcccg                                                     18

<210> SEQ ID NO 3
<211> LENGTH: 20
<212> TYPE: DNA
<213> ORGANISM: Norwalk-like Virus (GI)
<220> FEATURE:
<221> NAME/KEY: misc_feature
<222> LOCATION: (12)..(12)
<223> OTHER INFORMATION: n is a, c, g, or t

<400> SEQUENCE: 3
cgytggatgc gnttccatga                                                   20

<210> SEQ ID NO 4
<211> LENGTH: 20
<212> TYPE: DNA
<213> ORGANISM: Norwalk-like Virus (GI)
<220> FEATURE:
<221> NAME/KEY: misc_feature
<222> LOCATION: (12)..(12)
<223> OTHER INFORMATION: n is a, c, g, or t

<400> SEQUENCE: 4
cgytggatgc gntttcatga                                                   20

<210> SEQ ID NO 5
<211> LENGTH: 22
<212> TYPE: DNA
<213> ORGANISM: Norwalk-like Virus (GI)

<400> SEQUENCE: 5
ggbtcagctg trtttgcctc tg                                                22

<210> SEQ ID NO 6
<211> LENGTH: 22
<212> TYPE: DNA
<213> ORGANISM: Norwalk-like Virus (GI)

<400> SEQUENCE: 6
ggbtcagaag cattaacctc cg                                                22

<210> SEQ ID NO 7
<211> LENGTH: 22
<212> TYPE: DNA
<213> ORGANISM: Norwalk-like Virus (GI)

<400> SEQUENCE: 7
ggbtcagctg trttaacctc cg                                    22

<210> SEQ ID NO 8
<211> LENGTH: 22
<212> TYPE: DNA
<213> ORGANISM: Norwalk-like Virus (GI)

<400> SEQUENCE: 8
ggbtcagcat trttaacctc cg                                    22

<210> SEQ ID NO 9
<211> LENGTH: 22
<212> TYPE: DNA
<213> ORGANISM: Norwalk-like Virus (GI)

<400> SEQUENCE: 9
cttagacgcc atcatcatty ac                                    22

<210> SEQ ID NO 10
<211> LENGTH: 21
<212> TYPE: DNA
<213> ORGANISM: Norwalk-like Virus (GI)

<400> SEQUENCE: 10
tccttagacg ccatcatcat t                                     21

<210> SEQ ID NO 11
<211> LENGTH: 26
<212> TYPE: DNA
<213> ORGANISM: Norwalk-like Virus (GI)

<400> SEQUENCE: 11
taaatgatga tggcgtctaa ggacgc                                26

<210> SEQ ID NO 12
<211> LENGTH: 17
<212> TYPE: DNA
<213> ORGANISM: Norwalk-like Virus (GI)

<400> SEQUENCE: 12
tcgggcagga gatygcg                                          17

<210> SEQ ID NO 13
<211> LENGTH: 20
<212> TYPE: DNA
<213> ORGANISM: Norwalk-like Virus (GI)

<400> SEQUENCE: 13
agatygcgat cycctgtcca                                       20

<210> SEQ ID NO 14
<211> LENGTH: 20
<212> TYPE: DNA
<213> ORGANISM: Norwalk-like Virus (GI)

<400> SEQUENCE: 14
agatcgcggt ctcctgtcca                                       20

<210> SEQ ID NO 15
<211> LENGTH: 36
<212> TYPE: DNA
<213> ORGANISM: Artificial Sequence
<220> FEATURE:

<223> OTHER INFORMATION: probe

<400> SEQUENCE: 15
ccgtcgtaaa tgatgatggc gtctaaggac cgacgg          36

<210> SEQ ID NO 16
<211> LENGTH: 500
<212> TYPE: DNA
<213> ORGANISM: Norwalk-like Virus (GI)

<400> SEQUENCE: 16
aaattttaca gaaagatttc cagcaaggtc atacatgaaa tcaagactgg tggattggaa     60
atgtatgtcc caggatggca ggccatgttc cgctggatgc gcttccatga cctcggattg    120
tggacaggag atcgcgatct tctgcccgaa ttcgtaaatg atgatggcgt ctaaggacgc    180
tacatcaagc gtggatggcg ctagtggcgc tggtcagttg gtaccggagg ttaatgcttc    240
tgaccctctt gcaatggatc ctgtagcagg ttcttcgaca gcagtcgcga ctgctggaca    300
agttaatcct attgatccct ggataattaa taattttgtg caagcccccc aaggtgaatt    360 tactattttcc ccaaataata ccccggtga tgttttgttt gatttgagtt tgggtcccca    420
tcttaatcct ttcttgctcc atctatcaca aatgtataat ggttgggttg gtaacatgag    480
agtcaggatt atgctagctg                                                500

<210> SEQ ID NO 17
<211> LENGTH: 500
<212> TYPE: DNA
<213> ORGANISM: Norwalk-like Virus (GI)

<400> SEQUENCE: 17
aagttctaca ggaagatttc aagcaaagtc atccaggaaa ttaaaacagg gggccttgaa     60
atgtacgtgc caggatggca agccatgttc cgttggatgc ggttccatga ccttggtttg    120
tggacaggag atcgcaatct cctgcccgaa tttgtaaatg atgatggcgt ctaaggacgc    180
ccctcaaagc gctgatggcg caagcggcgc aggtcaactg gtgccggagg ttaatacagc    240 tgaccccttha cccatggaac ccgtggccgg gccaacaaca gccgtagcca ctgctgggca    300
agttaatatg attgatccct ggattgttaa taattttgtc cagtcaccac aaggtgagtt    360
cacaatttcc cctaataata ccccggtga tattttgttt gatttacaat taggtccaca    420 tctaaacccct ttcttgtcac atttgtccca aatgtataat ggctgggttg gaaatatgag    480
agttaggatt cttcttgctg                                                500

<210> SEQ ID NO 18
<211> LENGTH: 500
<212> TYPE: DNA
<213> ORGANISM: Norwalk-like Virus (GI)

<400> SEQUENCE: 18
aaattttaca ggaaaatatc tagcaaagtc atacatgaaa ttaagactgg tgggctggag     60
atgtatgtcc cagggtggca ggccatgttc cgctggatgc gcttccatga cctcggattg    120
tggacaggag atcgcaatct cctgcccgaa ttcgtaaatg atgatggcgt ctaaggacgc    180
tacgtcaagc gtggatggcg ccagtgcgtc ggttcagttg gtaccggagg ttaatgcttc    240
tgaccctctt gcaatggatc ctgtggcggg ttcttcaaca gcagttgcaa ccgctggaca    300
agttaaccct attgaccctt ggataatcaa taactttgtg caggctcccc aaggtgaatt    360
tactatttct ccaaataata ccccggtga tgttttgttt gatttgagtc taggccctca    420

-continued tcttaatccc ttcttgttac atttgtcaca aatgtataat ggctgggttg gcaacatgag 480
agttaggatt atgctggctg 500

<210> SEQ ID NO 19
<211> LENGTH: 500
<212> TYPE: DNA
<213> ORGANISM: Norwalk-like Virus (GI)

<400> SEQUENCE: 19
aagttttaca ggaaaatttc aggtagagtc atccaagaga tcaagacagg tggactggaa 60
atgtatgtgc caggctggca ggccatgttc cgctggatgc gttttcatga ccttggactt 120
tggacaggag atcgcgatct cctgcccgaa ttcgtaaatg atgatggcgt ctaaggacgc 180
cccaccatcg cctgatggcg ccagtggcgc tggccagcta gtgccggagg ttaatacagc 240
tgaccaaatt tcaatggatc ctgttgcggg tgcttctacc gcagttgcaa cagctgggca 300
agttaatatg attgatccat ggatattcaa caattttgtc caggcccccc agggtgaatt 360
taccatttct ccaaataata cccccggtga tattttattt gatttacaat tgggccccca 420
cttgaatcct ttcttagctc atttatcaca gatgtacaat ggatgggttg gcaatatgcg 480
ggtccgcata ttgctggcag 500

<210> SEQ ID NO 20
<211> LENGTH: 500
<212> TYPE: DNA
<213> ORGANISM: Norwalk-like Virus (GI)

<400> SEQUENCE: 20
aaattctaca gaaagatagc aagcagagtc atccaggaag ttaaagaagg ggggttagaa 60
atttacatcc ctgggtggca ggccatgttc cgctggatgc gcttccatga tctgagcatg 120
tggacagggg atcgcgatct cctgcccgat tatgtaaatg atgatggcgt ctaaggacgc 180
cccaacaaac atggatggca ccagtggtgc cggccagctg gtaccagagg caaacacagc 240
tgagcctatt tcaatggagc cagtggctgg ggctgcgaca gcagccgcaa ctgctggaca 300
agtaaatatg attgacccct ggataatgag taattatgta caagctcctc aaggagaatt 360
taccatatcg cccaacaata cacccggtga cattttattt gacctgcaat tgggcccaca 420
cctcaatcct ttcttgtccc atttagctca aatgtacaat ggttgggttg gaaatatgag 480
agtgaaggtg cttttggctg 500

<210> SEQ ID NO 21
<211> LENGTH: 500
<212> TYPE: DNA
<213> ORGANISM: Norwalk-like Virus (GI)

<400> SEQUENCE: 21
aagttttaca ggaagatagc tggtaaggtt atccaggaaa ttaagactgg tggtcttgaa 60
atgtacgtgc cgggttggca ggcaatgttc cgctggatgc gcttccatga tctcgggttg 120
tggacaggag atcgcaatct cctgcccgaa ttcgtaaatg atgatggcgt ctaaggacgc 180
tacaccaagc gcagatggcg cgaacggcgc cggtcagctc gtgccggagg ttaataatgc 240
tgaaccactg cctcttgatc ctgtggctgg ggcttctact gccttagcta ctgctggtca 300
agttaatatg attgatcctt ggattttcaa taactttgtc caagcccctc agggtgaatt 360
tacaatctcc cctaataata cccccggtga tatattattt gatttgcaat tgggacctca 420

-continued

```
cctcaatccc ttccttgccc atttgtcaca aatgtataat ggttgggttg gtaacatgcg        480
agtcagggtc atcctggcag                                                    500

<210> SEQ ID NO 22
<211> LENGTH: 451
<212> TYPE: DNA
<213> ORGANISM: Norwalk-like Virus (GI)

<400> SEQUENCE: 22
aaattttaca ggaaaatatc tagcaaagtc atacatgaaa ttaagactgg agggttggag         60
atgtatgtcc cagggtggca ggccatgttc cgctggatgc gcttccatga cctcggattg       120
tggacaggag atcgcaatct cctgcccgaa ttcgtaaatg atgatggcgt ctaaggacgc       180
tacgtcaagc gtggatggcg ccagtggcgc tggtcagttg gtaccggagg ttaatgcttc       240
tgaccctctt gcaatggatc ctgtggcggg ttcttcaaca gcagttgcaa ctgctgggca       300
agttaaccct attgaccctt ggataatcaa taactttgtg caggctcccc aaggtgaatt       360
tactatttct ccaaataata ccccggtga tgttttgttt gatttgagtc taggccctca       420
tcttaatccc ttccttgttac atttgtcaca a                                     451

<210> SEQ ID NO 23
<211> LENGTH: 452
<212> TYPE: DNA
<213> ORGANISM: Norwalk-like Virus (GI)

<400> SEQUENCE: 23
aaattttaca ggaaaatatc tagcaaagtc atacatgaaa ttaagactgg agggttggag         60
atgtatgtcc cagggtggca ggccatgttc cgctggatgc gcttccatga cctcggattg       120
tggacaggag atcgcaatct cctgcccgaa ttcgtaaatg atgatggcgt ctaaggacgc       180
tacgtcaagc gtggatggcg ccagtggcgc tggtcagttg gtaccggagg ttaatgcttc       240
tgaccctctt gcaatggatc ctgtggcggg ttcttcaaca gcagttgcaa ctgctgggca       300
agttaaccct attgaccctt ggataatcaa taactttgtg caggctcccc aaggtgaatt       360
tactatttct ccaaataata ccccggtga tgttttgttt gatttgagtc taggccctca       420
tcttaatccc ttccttgttac atttgtcaca ac                                    452

<210> SEQ ID NO 24
<211> LENGTH: 442
<212> TYPE: DNA
<213> ORGANISM: Norwalk-like Virus (GI)
<220> FEATURE:
<221> NAME/KEY: misc_feature
<222> LOCATION: (441)..(442)
<223> OTHER INFORMATION: n is a, c, g, or t

<400> SEQUENCE: 24
aagttctaca ggaagatctc cagtaaagtc atacaggaga taaagactgg tggtttggaa         60
atgtatgtgc caggttggca ggccatgttt cgctggatgc gcttccatga tctcggattg       120
tggacaggag atcgcaatct cctgcccgaa ttcgtaaatg atgatggcgt ctaaggacgc       180
tacaccaagc gcagatggcg ccactggcgc cggccagctg gtaccggagg ttaatacagc       240
tgaccctata cctattgacc ctgtggctgg ctcttccaca gccttgcca cagcaggcca       300 ggttaatttg attgatccct ggataatcaa taattttgtg caagcccccc agggcgagtt       360
tacaatatcc ccaaacaata ccccggtga tgtgcttttt gatttgcagt tagggcctca       420
tttgaaccct ttcctctccc nn                                                442
```

<210> SEQ ID NO 25
<211> LENGTH: 451
<212> TYPE: DNA
<213> ORGANISM: Norwalk-like Virus (GI)

<400> SEQUENCE: 25

| | | | | | |
|---|---|---|---|---|---|
| aagttctata | gaaagatagc | tagtagggtg | atccaggagg | ttaaggaagg | aggattggaa | 60 |
| atttacattc | ctgggtggca | ggccatgttc | cgctggatgc | gattccatga | tttgagcttg | 120 |
| tggacaggag | accgcgatct | cttgcccgat | tatgtaaatg | atgatggcgt | ctaaggacgc | 180 |
| cccaacaaac | atggatggca | ctagtggtgc | cggtcagctg | gtaccagagg | caaatacagc | 240 |
| tgaacctata | tcaatggacc | cagtggctgg | agccgcaaca | gcggttgcaa | ctgctggaca | 300 |
| aattaatatg | attgacccct | ggataatgag | taattttgtg | caggccccac | aaggggagtt | 360 |
| taccgtctca | cccaaataaca | cccctggaga | tgttttattt | gatctacaat | tgggacctca | 420 |
| attaaatcca | ttcctcgccc | tgctagccca | a | | | 451 |

<210> SEQ ID NO 26
<211> LENGTH: 442
<212> TYPE: DNA
<213> ORGANISM: Norwalk-like Virus (GI)
<220> FEATURE:
<221> NAME/KEY: misc_feature
<222> LOCATION: (441)..(442)
<223> OTHER INFORMATION: n is a, c, g, or t

<400> SEQUENCE: 26

| | | | | | |
|---|---|---|---|---|---|
| aagttttaca | ggaaaatctc | cagtaaagtt | atacaggaga | taaagactgg | tggtttggaa | 60 |
| atgtatgtgc | caggctggca | ggccatgttc | cgctggatgc | gcttccatga | tctcggattg | 120 |
| tggacaggag | atcgcaatct | cctgcccgaa | ttcgtaaatg | atgatggcgt | ctaaggacgc | 180 |
| tacaccaagc | gcagatggcg | ccactggcgc | cggccagctg | gtaccggagg | ttaatacagc | 240 |
| tgaccctata | cccattgacc | ctgtggctgg | ctcctctaca | gcacttgcca | ctgcaggcca | 300 |
| ggttaatttg | attgatccct | ggataatcaa | taattttgtg | caagcccccc | agggcgaatt | 360 |
| cacaatatcc | ccaaataata | ccccggtga | tgtgcttttt | gatttgcaat | taggacctca | 420 |
| tttaaaccct | ttcctctccc | nn | | | | 442 |

<210> SEQ ID NO 27
<211> LENGTH: 450
<212> TYPE: DNA
<213> ORGANISM: Norwalk-like Virus (GI)

<400> SEQUENCE: 27

| | | | | | |
|---|---|---|---|---|---|
| aaattctaca | gaaagatagc | aagcagagtc | atccaggaag | tcaaagaagg | ggggttagag | 60 |
| atttacatcc | ctgggtggca | ggccatgttc | cgctggatgc | gcttccatga | tctgagcatg | 120 |
| tggacagggg | atcgcgatct | cctgcccgat | tatgtaaatg | atgatggcgt | ctaaggacgc | 180 |
| cccaacaaac | atggatggca | ccagtggtgc | cggccagctg | gtaccagagg | caaacacagc | 240 |
| tgagcctatt | gctatggatc | cagtagttgg | tgctgctacg | gcagttgcca | ctgctggtca | 300 |
| agtaaatatg | attgacccct | ggattatgag | taattttgtt | caagcacccc | aaggagagtt | 360 |
| tacaatttca | cccaataaca | cacctggtga | tattttgttt | gatttacaat | taggacctca | 420 |
| attaaacccc | tttttgtctc | atttagcaca | | | | 450 |

<210> SEQ ID NO 28

<211> LENGTH: 452
<212> TYPE: DNA
<213> ORGANISM: Norwalk-like Virus (GI)

<400> SEQUENCE: 28

```
aagttctata gaaaaatagc cagcagagtc atccaagaaa ttaagacggg gggcttggaa    60
atgtatgtgc caggttggca ggccatgttc cgctggatgc gtttccatga ccttgggctt   120
tggacagggg atcgcaatct gctgcccgaa ttcgtgaatg atgatggcgt ctaaggacgc   180
cccaacatcc cctgatggcg ctagtggcgc cggccagctg gtaccggagg ctaatacagc   240
tgagcaaatt tcaatggacc ctgttgcggg tgcttcaaca gcagtcgcaa cggctggaca   300
agttaatatg attgacccat ggatttttaa taactttgtc caggcacccc aaggagaatt   360
cactatttcc cctaataata ccccggtga tattttgttt gatctacaat taggacccca   420
ccttaaccca tttctggctc atctttcgca ga                                 452
```

<210> SEQ ID NO 29
<211> LENGTH: 443
<212> TYPE: DNA
<213> ORGANISM: Norwalk-like Virus (GI)
<220> FEATURE:
<221> NAME/KEY: misc_feature
<222> LOCATION: (442)..(443)
<223> OTHER INFORMATION: n is a, c, g, or t

<400> SEQUENCE: 29

```
aagttttaca ggaaaatctc cagtaaagtt atacaggaga taaagactgg tggtttggaa    60
atgtatgtgc caggctggca ggccatgttc cgctggatgc gcttccatga tctcggattg   120
tggacaggag atcgcaatct cctgcccgaa ttcgtaaatg atgatggcgt ctaaggacgc   180
cacaccaagc gcagatggcg ccactggcgc cggccagctg gtaccggagg ttaatacagc   240
tgaccctata cccattgacc ctgtggctgg ctcctctaca gcacttgcca ctgcaggcca   300
ggttaatttg attgatccct ggataatcaa taattttgtg caagcccccc agggcgaatt   360
cacaatatcc ccaaataata ccccggtga tgtgcttttt gatttgcagt taggacctca   420
tttaaacccct ttcctctccc tnn                                          443
```

<210> SEQ ID NO 30
<211> LENGTH: 386
<212> TYPE: DNA
<213> ORGANISM: Norwalk-like Virus (GI)
<220> FEATURE:
<221> NAME/KEY: misc_feature
<222> LOCATION: (384)..(384)
<223> OTHER INFORMATION: n is a, c, g, or t

<400> SEQUENCE: 30

```
gaaatgtatg tgccaggctg gcaggccatg ttccgctgga tgcgcttcca tgatctcgga    60
ttgtggacag gagatcgcaa tctcctgccc gaattcgtaa atgatgatgg cgtctaagga   120
cgctacacca agcgcagatg gcgccactgg cgccggccag ctggtaccgg aggttaatac   180
agctgaccct atacccattg accctgtggc tggctcctct acagcacttg ccactgcagg   240
ccaggttaat ttgattgatc cctggataat caataatttt gtgcaagccc ccagggcga   300
attcacaata tccccaaata taccccccgg tgatgtgctt tttgatttgc aattaggacc   360
tcatttaaac cctttcctct cccncc                                        386
```

<210> SEQ ID NO 31
<211> LENGTH: 351

<212> TYPE: DNA
<213> ORGANISM: Norwalk-like Virus (GI)

<400> SEQUENCE: 31

```
tttccatgac ttgagcttgt ggacaggaga tcgcaatctc ctgcccgatt atgtaaatga      60
tgatggcgtc taaggacgcc ccctcaaaca tggatggcac tagtggtgcc ggtcagctgg     120
ttccagaggt taatgcagct gaaccnctac cccttgagcc ggtggtgggt gccgcaactg     180
cggcggccac tgctgggcaa gttaatttaa tagacccctg gatcatgaat aattttgtcc     240
aagcccctga gggcgaattc actatctccc ctaataatac ccctggagat attttatttg     300
atttgcaatt gggaccacat cttaaccctt tccttcaaca tttgtctcaa a              351
```

<210> SEQ ID NO 32
<211> LENGTH: 351
<212> TYPE: DNA
<213> ORGANISM: Norwalk-like Virus (GI)

<400> SEQUENCE: 32

```
cttccatgac ttcggattgt ggacaggaga tcgcaatctc ctgcccgaat tcgtaaatga      60
tgatggcgtc taaggacgct acgtcaagcg tggatggcgc cagtggcgct ggtcagttga     120
taccggaggt taatgcttct gaccctcttg caatggatcc tgtggcgggt tcttcaacag     180
cagttgcaac tgctgggcaa gttaaccta ttgacccttg gataatcaat aactttgtgc      240
aggctcccca aggtgaattt actatttctc caaataatac ccccggtgat gttttgtttg     300
atttgagtct aggccctcat cttaatccct tcttgttaca tttgtcacaa a              351
```

<210> SEQ ID NO 33
<211> LENGTH: 351
<212> TYPE: DNA
<213> ORGANISM: Norwalk-like Virus (GI)

<400> SEQUENCE: 33

```
cttccatgac ctcggattgt ggacaggaga tcgcaatctc ctgcccgaat tcgtaaatga      60
tgatggcgtc taaggacgct acgtcaagcg tggatggcgc cagtggcgct ggtcagttgg     120
taccggaggt taatgcttct gaccctcttg caatggatcc tgtggcgggt tcttcaacag     180
cagttgcaac tgctgggcaa gttaaccta ttgacccttg gataatcaat aactttgtgc      240
aggctcccca aggtgaattt actatttctc caaataatac ccccggtgat gttttgtttg     300
atttgagtct aggcctcat cttaatccct tcttgttaca tttgtcacaa a               351
```

<210> SEQ ID NO 34
<211> LENGTH: 351
<212> TYPE: DNA
<213> ORGANISM: Norwalk-like Virus (GI)

<400> SEQUENCE: 34

```
gttccatgac cttggtttgt ggacaggaga tcgcaatctc ctgcccgaat ttgtaaatga      60
tgatggcgtc taaggacgcc cctcaaagcg ctgatggcgc aagcggcgca ggtcaactgg     120
tgccggaggt taatacagct gacccnctac ccatggaacc cgtggctggg ccaacaacag     180
ccgtagccac tgctgggcaa gttaatatga ttgatccctg gattgttaat aattttgtcc     240
agtcacctca aggtgagttt acaatttccc ctaataatac ccccggtgat attttgtttg     300
atttacaatt aggacctcaa ttaaaccct ttttgtctca tttagcacaa a               351
```

<210> SEQ ID NO 35

-continued

<211> LENGTH: 351
<212> TYPE: DNA
<213> ORGANISM: Norwalk-like Virus (GI)

<400> SEQUENCE: 35
gttccatgac cttggtttgt ggacaggaga tcgcaatctc ctgcccgaat ttgtaaatga 60
tgatggcgtc taaggacgcc cctcaaagcg ctgatggcgc aagcggcgca ggtcaactgg 120
tgccggaggt taatacagct gaccccttac ccatggaacc cgtggctggg ccaacaacag 180
ccgtagccac tgctgggcaa gttaatatga ttgatccctg gattgttaat aattttgtcc 240
agtcacctca aggtgagttt acaatttccc ctaataatac ccccggtgat attttgtttg 300
atttacaatt aggtccacat ctaaaccctt tcttgtcgca tttgtcccaa a 351

<210> SEQ ID NO 36
<211> LENGTH: 291
<212> TYPE: DNA
<213> ORGANISM: Norwalk-like Virus (GI)

<400> SEQUENCE: 36
tgatggcgtc taaggacgct acaccaagcg cagatggcgc cactggcgcc ggccagctgg 60
taccggaggt taatacagct gaccctatac ccattgaccc tgtggctggc tcctctacag 120
cacttgccac tgcaggccag gttaatttga ttgatccctg gataatcaat aattttgtgc 180
aagcccccca gggtgaattc acaatatccc caaataatac ccccggtgat gtgctttttg 240
atttgcagtt aggacctcat ttaaaccctc tcctctccca tctctctcag a 291

<210> SEQ ID NO 37
<211> LENGTH: 351
<212> TYPE: DNA
<213> ORGANISM: Norwalk-like Virus (GI)

<400> SEQUENCE: 37
cttccatgat ctcggattgt ggacaggaga tcgcaatctc ctgcccgaat tcgtaaatga 60
tgatggcgtc taaggacgct acaccaagcg cagatggcgc cactggcgcc ggccagctgg 120
taccggaggt taatacagct gaccctatac ccattgaccc tgtggctggc tcctctacag 180
cacttgccac tgcaggccag gttaatttta ttgatccctg gataatcaat aattttgtgc 240
aagcccccca gggtgaattc acaatatccc caaataatac ccccggtgat gtgctttttg 300
atttgcagtt aggacctcat ttaaaccctt tcctctccca tctctctcag a 351

<210> SEQ ID NO 38
<211> LENGTH: 291
<212> TYPE: DNA
<213> ORGANISM: Norwalk-like Virus (GI)

<400> SEQUENCE: 38
tgatggcgtc taaggacgct acaccaagcg cagatggcgc cactggcgcc ggccagctgg 60
taccggaggt taatacagct gaccctatac ccattgaccc tgtggctggc tcctctacag 120
cacttgccac tgcaggccag gttaatttga ttgatccctg gataatcaat aattttgtgc 180
aagcccccca gggtgaattc acaatatccc caaataatac ccccggtgat gtgctttttg 240
atttgcagtt aggacctcat ttaaaccctt tcctctccca tctctctcag a 291

<210> SEQ ID NO 39
<211> LENGTH: 351
<212> TYPE: DNA
<213> ORGANISM: Norwalk-like Virus (GI)

<400> SEQUENCE: 39

| cttccatgat | ctcggattgt | ggacaggaga | tcgcaatctc | ctgcccgaat | tcgtaaatga | 60 |
| tgatggcgtc | taaggatgct | acaccaagcg | cagatggcgc | cactggcgcc | ggccagctgg | 120 |
| taccggaggt | taatacagct | gaccctatac | ccattgaccc | tgtggctggc | tcctctacag | 180 |
| cacttgccac | tgcaggccag | gttaatttga | ttgatccctg | gataatcaat | aattttgtgc | 240 |
| aagccccca | gggtgaattc | acaatatccc | caaataatac | ccccggtgat | gtgcttttg | 300 |
| atttgcagtt | aggacctcat | ttaaacccct | tcctctccca | tctctctcag | a | 351 |

<210> SEQ ID NO 40
<211> LENGTH: 348
<212> TYPE: DNA
<213> ORGANISM: Norwalk-like Virus (GI)

<400> SEQUENCE: 40

| cttccatgat | ctcggattgt | ggacaggaga | tcgcaatctc | ctgcccgaat | tcgtaaatga | 60 |
| tgatggcgtc | taaggacgcc | acaccaagcg | cagatggcgc | cactggcgcc | ggccagctgg | 120 |
| taccggaggt | taatacagct | gaccctatac | ccattgaccc | tgtggctggc | tcctctacag | 180 |
| cacttgccac | tgcaggccag | gttaatttga | ttgatccctg | gataatcaat | aattttgtgc | 240 |
| aagccccca | gggcgaattc | acaatatccc | caaataatac | ccccggtgat | gtgcttttg | 300 |
| atttgcagtt | aggacctcat | ttaaacccct | tcctctccca | tctctctc | | 348 |

<210> SEQ ID NO 41
<211> LENGTH: 351
<212> TYPE: DNA
<213> ORGANISM: Norwalk-like Virus (GI)

<400> SEQUENCE: 41

| gttccatgat | cttggcttgt | ggacaggaga | tcgcaatctc | ctgcccgaat | ttgtaaatga | 60 |
| tgatggcgtc | taaggacgcc | cctcaaagcg | ctgatggcgc | aagcggcgca | ggtcaactgg | 120 |
| tgccggaggt | taatacagct | gaccccttac | ccatggaacc | cgtggctggg | ccaacaacag | 180 |
| ccgtagccac | tgctggacaa | gttaatatga | ttgatccatg | gattgttaac | aattttgtcc | 240 |
| agtcaccaca | aggtgagttt | acaatttccc | ctaataatac | ccccggtgat | attttgtttg | 300 |
| atttacaatt | aggtccacat | ctaaatccct | tcttgtcaca | tttatctcag | a | 351 |

<210> SEQ ID NO 42
<211> LENGTH: 348
<212> TYPE: DNA
<213> ORGANISM: Norwalk-like Virus (GI)

<400> SEQUENCE: 42

| cttccatgac | ctcggattgt | ggacaggaga | tcgcaatctc | ctgcccgaat | tcgtaaatga | 60 |
| tgatggcgtc | taaggacgct | acaccaagcg | cagatggcgc | gaatggcgcc | ggccagcttg | 120 |
| tgccggaggt | taataatgct | gaaccactgc | cacttgatcc | agtggcggga | gcttccaccg | 180 |
| ctcttgccac | tgctggacaa | gttaatatga | ttgacccatg | gattttcaac | aattttgttc | 240 |
| aggctcccca | gggtgaattt | accatatctc | caaataatac | ccccggcgat | attctttttg | 300 |
| atttgcaatt | aggcccacac | ctaaaccctt | tcctagcaca | tttatccc | | 348 |

<210> SEQ ID NO 43
<211> LENGTH: 348
<212> TYPE: DNA

<213> ORGANISM: Norwalk-like Virus (GI)

<400> SEQUENCE: 43

```
cttccatgat ctcggattgt ggacaggaga tcgcaatctc ctgcccgaat tcgtaaatga      60
tgatggcgtc taaggacgcc acaccaagcg cagatggcgc cactggcgcc ggccagctgg     120
taccggaggt taatacagct gaccctatac ccattgaccc tgtggctggc tcctctacag     180
cacttgccac tgcaggccag gttaatttga ttgatccctg gataatcaat aattttgtgc     240
aagcccccca gggcgaattc acaatatccc caaataatac ccccggtgat gtgcttttg     300
atttgcagtt aggacctcat ttaaaccctt tcctctccca tctctctc                 348
```

<210> SEQ ID NO 44
<211> LENGTH: 348
<212> TYPE: DNA
<213> ORGANISM: Norwalk-like Virus (GI)

<400> SEQUENCE: 44

```
cttccatgat ctcggattgt ggacaggaga tcgcaatctc ctgcccgaat tcgtaaatga      60
tgatggcgtc taaggacgcc acaccaagcg cagatggcgc cactggcgcc ggccagctgg     120
taccggaggt taatacagct gaccctatac ccattgaccc tgtggctggc tcctctacag     180
cacttgccac tgcaggccag gttaatttga ttgatccctg gataatcaat aattttgtgc     240
aagcccccca gggcgaattc acaatatccc caaataatac ccccggtgat gtgcttttg     300
atttgcagtt aggacctcat ttaaaccctt tcctctccca tctctctc                 348
```

<210> SEQ ID NO 45
<211> LENGTH: 348
<212> TYPE: DNA
<213> ORGANISM: Norwalk-like Virus (GI)

<400> SEQUENCE: 45

```
cttccatgat ctcggattgt ggacaggaga tcgcaatctc ctgcccgaat tcgtaaatga      60
tgatggcgtc taaggacgcc acaccaagcg cagatggcgc cactggcgcc ggccagctgg     120
taccggaggt taatacagct gaccctatac ccattgaccc tgtggctggc tcctctacag     180
cacttgccac tgcaggccag gttaatttga ttgatccctg gataatcaat aattttgtgc     240
aagcccccca gggcgaattc acaatatccc caaataatac ccccggtgat gtgcttttg     300
atttgcagtt aggacctcat ttaaaccctt tcctctccca tctctctc                 348
```

<210> SEQ ID NO 46
<211> LENGTH: 348
<212> TYPE: DNA
<213> ORGANISM: Norwalk-like Virus (GI)

<400> SEQUENCE: 46

```
cttccatgat ctcggattgt ggacaggaga tcgcaatctc ctgcccgaat tcgtaaatga      60
tgatggcgtc taaggacgcc acaccaagcg cagatggcgc cactggcgcc ggccagctgg     120
taccggaggt taatacagct gaccctatac ccattgaccc tgtggctggc tcctctacag     180
cacttgccac tgcaggccag gttaatttga ttgatccctg gataatcaat aattttgtgc     240
aagcccccca gggcgaattc acaatatccc caaataatac ccccggtgat gtgcttttg     300
atttgcagtt aggacctcat ttaaaccctt tcctctccca tctctctc                 348
```

<210> SEQ ID NO 47
<211> LENGTH: 351

```
<212> TYPE: DNA
<213> ORGANISM: Norwalk-like Virus (GI)

<400> SEQUENCE: 47
cttccatgat ctcggattgt ggacaggaga tcgcaatctc ctgcccgaat tcgtaaatga      60
tgatggcgtc taaggacgct acaccaagcg cagatggcgc cactggcgcc ggccagctgg     120
taccggaggt taatacagct gaccctatac ccattgaccc tgtggctggc tcctctacag     180
cacttgccac tgcaggccag gttaatttga ttgatccctg gataatcaat aattttgtgc     240
aagcccccca gggcgaattc acaatatccc caaataatac cccggtgrt gtgcttttg       300
atttgcagtt aggacctcat ttaaaccctt tcctctccca tctctctcag a              351

<210> SEQ ID NO 48
<211> LENGTH: 343
<212> TYPE: DNA
<213> ORGANISM: Norwalk-like Virus (GI)

<400> SEQUENCE: 48
atgatgatgg cgtctaagga cgtcccctca aacatggatg gcwctagtgg tgccggtcag      60
ctggttccag aggttaatgc agctgaaccc ctacctcttg aaccggtagt gggcgccgca     120
accgcggcgg ccactgctgg acaagttaat ttaatagacc cctggattat gaataatttt     180
gtccaagccc ctgagggtga atttaccatt tcacccaaca ataccctgg agatattctg      240
tttgatctgc atttgggacc acatcttaat cccttcctcc aacatttatc ccaaatgtat     300
aatggctggg tggggaacgt gagagtcaga gtcatgcttg cgg                       343

<210> SEQ ID NO 49
<211> LENGTH: 343
<212> TYPE: DNA
<213> ORGANISM: Norwalk-like Virus (GI)

<400> SEQUENCE: 49
atgatgatgg cgtctaaggg cgcccctcaa agcgctgatg gctcaagcgg cgcaggtcaa      60
ctggtgccgg aggttaatac agctgacccc ttacccatgg aaccgtggc tgggccaaca      120
acagccgtag ccactgctgg gcaagttaat atgattgatc cctggattgt taataatttt     180
gtccagtcac acaaggtga gtttacaatt tccctaata atacccccgg cgatattttg       240
tttgatttac aattaggtcc acatctaaac cctttcttgt cacatttgtc ccaaatgtat     300
aatggctggg ttggaaacat gagagttagg attcttcttg ctg                       343

<210> SEQ ID NO 50
<211> LENGTH: 343
<212> TYPE: DNA
<213> ORGANISM: Norwalk-like Virus (GI)

<400> SEQUENCE: 50
atgatgatgg cgtctaaggg cgccccaaca aacatggatg gcaccagtgg tgctggccag      60
ctggtaccag aggcaaatac agctgagcct atatcaatgg agcctgtggc tggggcagca     120
acagctgccg caaccgctgg ccaagttaat atgattgacc cctggataat gaataattat     180
gtgcaagccc ctcaaggtga attcactata tcgcctaata ataccaccagg tgatattttg    240
tttgatctac aattaggccc ccatctcaat cctttcttat cccatttggc ccaaatgtat     300
aacggttggg ttggcaatat gagagtgaag gtcctattgg ctg                       343

<210> SEQ ID NO 51
```

-continued

<211> LENGTH: 343
<212> TYPE: DNA
<213> ORGANISM: Norwalk-like Virus (GI)

<400> SEQUENCE: 51
atgatgatgg cgtctaagga cgctacacca agcgcagatg gcgcgaatgg cgccggtcag 60
cttgtgccgg aggttaataa tgctraacca ctgccacttg atccagtggc gggagcttct 120
accgctctag ccactgctgg acaagttaat atgattgacc catggatttt caacaacttt 180
gttcaggccc cccagggtga atttaccata tccccaaata atacccccgg cgatattctt 240
tttgatttgc aattaggccc acrcctaaac cctttcctag cacatttatc ccagatgtat 300
aatggttggg ttggtaatat gcgagtcagg gtcatcttgg ctg 343

<210> SEQ ID NO 52
<211> LENGTH: 343
<212> TYPE: DNA
<213> ORGANISM: Norwalk-like Virus (GI)

<400> SEQUENCE: 52
atgatgatgg cgtctaagga tgccccaaca tcccctgatg gcgccagtgt gcgccggcag 60
ctggtaccgg acgctaatac agctgagcaa atttcaatgg accctgttgc gggtgcttca 120
acagcactcg caacggctgg gcaagttaat atgattgacc catggatttt caataacttt 180
gtccaggcac cccaaggaga attcactatt tcccctaata atacccccgg tgataatttg 240
tttgacttac aattaggwcc ccatcttaat ccatttctag cccacctctc acagatgtat 300
aatggttggg tcggcaacat gcgtgtgcgc atattgttgg ccg 343

<210> SEQ ID NO 53
<211> LENGTH: 343
<212> TYPE: DNA
<213> ORGANISM: Norwalk-like Virus (GI)

<400> SEQUENCE: 53
atgatgatgg cgtctaagga cgctacacca agcgcagatg gcgccactgg cgccggccag 60
ctggtaccgg aggttaatac agctgaccct atacccattg accctgtggc tggctcctct 120
acagcacttg ccactgcagg ccaggttaat ttgattgatc cctggataat caataatttt 180
gtgcaagccc cccagggcga attcacaata tccccaaata atacccccgg tgatgtgctt 240
tttgatttgc agttaggacc tcatttaaac cctttcctct cccatctctc tcagatgtat 300
aatggctggg tgggcaacat gcgagtgcgt gttgtcttgg ctg 343

<210> SEQ ID NO 54
<211> LENGTH: 343
<212> TYPE: DNA
<213> ORGANISM: Norwalk-like Virus (GI)

<400> SEQUENCE: 54
atgatgatgg cgtctaagga cgctacacca agcgcagatg gcgccactgg cgccggccag 60
ctggtaccgg aggttaatac agctgacccc atacctattg accctgtggc tggctcctcc 120
acggcccttg ccacagcagg ccaggttaat ttgattgatc cttggataat caataatttt 180
gtgcaagccc ctcagggcga attcacaata tccccaaaca atacccccgg tgatgtgctt 240
tttgatttac aattgggacc ccatttaaat ccattccttt cccacctttc tcagatgtat 300
aatggctggg tgggcaacat gcgagtgcgt gttgtcttgg ctg 343

-continued

```
<210> SEQ ID NO 55
<211> LENGTH: 29
<212> TYPE: DNA
<213> ORGANISM: Artificial Sequence
<220> FEATURE:
<223> OTHER INFORMATION: probe

<400> SEQUENCE: 55
ccgctgtcgg gcaggagaty gcgcagcgg                                    29

<210> SEQ ID NO 56
<211> LENGTH: 32
<212> TYPE: DNA
<213> ORGANISM: Artificial Sequence
<220> FEATURE:
<223> OTHER INFORMATION: probe

<400> SEQUENCE: 56
ccgctgagat ygcgatcycc tgtccacagc gg                                32

<210> SEQ ID NO 57
<211> LENGTH: 32
<212> TYPE: DNA
<213> ORGANISM: Artificial Sequence
<220> FEATURE:
<223> OTHER INFORMATION: probe

<400> SEQUENCE: 57
ccgctgagat cgcggtctcc tgtccacagc gg                                32
```

METHOD OF DETECTING NORWALK-LIKE VIRUS (GI)

TECHNICAL FIELD

The present invention relates to a method of detecting a virus.

BACKGROUND ART

The term "food poisoning" generally brings to mind bacterial food poisoning caused by bacteria such as *Salmonella, Vibrio parahaemolyticus,* and pathogenic *E. coli,* or natural toxin food poisoning caused by natural toxins contained in, for example, globefish or mushrooms. In addition, a very large number of food poisoning cases are caused by viruses, such as Norwalk-like viruses (hereinafter referred to as NLVs), rotavirus, astrovirus, enterovirus, adenovirus, and hepatitis A virus. Recent epidemiological research has revealed that, among other viruses, Norwalk-like viruses are typical food-poisoning viruses.

Norwalk virus was first identified in 1972 after an outbreak of gastrointestinal illness in the U.S.A. Under an electron microscope, the virus is observed as a small spherical virus of about 30 nm in diameter having an unclear surface structure, and since then viruses having similar shapes have been collectively called "small round structured viruses" (SRSVs). In the meantime, in 1974, calicivirus, which had been well known in veterinary medicine and which measures about 30 nm in diameter and assumes a unique surface structure resembling a "Star of David," was first identified in a human patient; specifically, in a patient suffering winter vomiting disease, which was at that time epidemic in Britain. Since then, viruses having a shape similar to the above have been called classical human caliciviruses.

These viruses are very difficult to grow in tissue culture cells or in experimental animals, and therefore, for some time the only feasible method was to isolate and culture the viruses on volunteers by use of stool specimens. Thus, characterization of the viruses was quite difficult. In 1990, a research group led by X. Jiang cloned the genome of Norwalk virus, and since then, gene analysis of these viruses has been energetically performed. Such efforts have revealed that an SRSV and a classical human calicivirus both belong to the family of Caliciviridae, having a single stranded "plus" RNA (plus-stranded). In the XIth International Congress of Virology, the family Caliciviridae was reported to comprise four different genera.

Thus, a group of viruses that had been called SRSVs was determined to belong to the genus Norwalk-like viruses (NLVs), and another group that had been called classical human caliciviruses was determined to belong to the genus Sapporo-like viruses (SLVs). Moreover, from an accumulation of data of genomic nucleotide sequences of viruses collected from a vast number of clinical specimens, NLVs have been confirmed to be classified into two genogroups I and II; i.e., genogroup I (GI) encompassing Norwalk viruses and Southampton viruses, and similar viruses; and genogroup II (GII) encompassing Hawaii viruses, Snow Mountain viruses, and similar viruses.

NLV infections in humans primarily occur by the mediation of foods (fish, shellfish, and water). Most of the viral food-poisoning cases that frequently occur during winter are believed to be caused by ingestion of shellfish such as oysters, and in fact, in a great number of study reports, oysters are identified as the source of infection with NLVs. Some reports describe that ingestion of a sandwich contaminated with NLVs caused infection. Thus, presumably, NLV infection readily spreads through feces from an infected patient. (This virus is known to have strong infectivity and to cause infection even in a case where several to about one hundred viruses are present in a food product).

Once food poisoning has occurred, needless to say, identification of the cause and the contamination source is a critical issue. That is, the food-poisoning patients must be treated as quickly as possible through appropriate selection of a therapeutic method, which would be realized by identifying the cause of the food poisoning, and simultaneously, spreading of food poisoning must be stopped by identifying the contamination source as early as possible.

In particular, in order to identify the cause and the contamination source of food poisoning caused by pathogenic microorganisms, the following are required: detection and identification of the pathogenic microorganism that caused the illness (i.e., identification of the cause of the food poisoning); and identification of the food and the food manufacturing facility that caused the food poisoning, on the basis of, for example, the diet history of the patient suffering food poisoning (identification of the contamination source of the food poisoning).

Conventionally, an electron microscope has been employed to detect the above-mentioned NLVs. However, methods employing an electron microscope require an intricate procedure, and in addition, rapid and accurate detection of viruses is difficult in cases where the quantity of the viruses is small. In particular, since a very small amount of NLV particles exhibit infectivity, rapid and accurate detection of NLVs in, for example, contaminated foods is keenly desired, and yet, realization has been difficult. Moreover, detection methods employing an electron microscope require a large facility for accommodating the electron microscope, and thus, detection through electron microscopy has been possible in only a limited number of facilities.

By keeping pace with the recent progress in gene analysis techniques, more sensitive, more rapid gene analysis through RT-PCR has now been performed frequently. In order to detect a virus through use of this method, primers for amplifying a specific region of the gene (hereinafter referred to as gene amplification primers) and primers used in the process of detecting a gene amplification product of interest on the basis of the presence of the specific region serving as an index (hereinafter referred to as detection primers) must be designed and employed. Particularly in the case of viruses such as NLVs, design of such primers encounters a problem which is very difficult to solve. That is, viruses easily undergo mutation and therefore, even in the case in which the virus responsible for the previous outbreak of food poisoning falls within the same group of the virus that is now epidemic, there is a high risk that detection may be disabled unless primers different from those employed for detection of the virus in previous outbreaks are used for the current food poisoning. Needless to say, attaining accurate identification of the source of contamination will still require use of detection primers each individually specific to viral mutation variants. However, this would only be required for the purpose of verification and would suffice if performed after identification of the causative virus of the food poisoning and identification of the source of infection is almost complete. More importantly, rapid identification should be given a high priority so as to establish a therapeutic regimen for the food-poisoning patient and to prevent spreading of contamination.

In order to solve the above problem, a need exists for discovering a highly conserved region in genes of a virus of interest, and designing, among other things, detection primers which correspond to the region, thus providing means for detecting the virus through use of such tools.

Accordingly, an object of the present invention is to identify a highly conserved region in genes of NLVs, and, on the basis of the information thus obtained, to provide rapid, accurate means for detecting NLVs.

DISCLOSURE OF THE INVENTION

In order to attain the above object, the present inventors have conducted careful studies and have successfully identified a highly conserved region (bridging the vicinity of the C-terminus of the ORF 1 region and the vicinity of the N-terminus of the ORF 2 region) in a gene of NLV genogroup I, and, on the basis of this finding, have devised rapid, accurate means for detecting viruses belonging to genogroup I of NLVs, among other NLVs, leading to completion of the present invention.

First, there will be described an essential discovery that constitutes the basis for the present invention; i.e., a highly conserved region commonly found in genes of Norwalk-like viruses (NLVs) belonging to genogroup I (hereinafter also referred to as NLVs (GI)).

In order to identify the above-mentioned highly conserved region in the gene of an NLV (GI), the present inventors performed the following test.

Details of the Test (1) Stool Specimens and Preparation of RNA Samples

Gene analysis of NLVs (GI) was performed on stool specimens collected from 44 cases of non-bacterial gastroenteritis from which NLV particles were detected through electron microscopy in the Saitama Institute of Public Health during 1998–2000.

Briefly, each of the stool specimens was suspended in sterilized distilled water so as to attain a concentration of about 10% (W/V), and the suspension was subjected to centrifugation at 3000×g for 5 minutes. From the supernatant (140 μL), nucleic acid was extracted in accordance with the manufacturer's protocol of an RNA extraction kit (QIA Viral RNA, Qiagen), and suspended in 50 μL sterilized distilled water, whereby an RNA sample was obtained.

(2) Determination of Full Length Sequences of NLV Genes and Analysis of the Genes cDNA was synthesized from each of the thus-prepared RNA samples by use of an oligo dT primer, and amplified through LongRT-PCR. The nucleotide sequence of each of the gene amplification products was determined through direct sequencing by use of the primer walking method (Nucleic Acids Res. 1989 17(15): 6087–6102). Sequencing of the genomic 5'-terminus was performed using three types of RACE (rapid amplification of cDNA ends).

Through the gene analysis employing the above RNA samples, the entire nucleotide sequence of a new NLV strain (GI, SzUG1) was determined (registration No. GenBank AB09774), and partial nucleotide sequences (26 sequences) of 17 strains were also determined (#P1, #4a, #4b, #4c, #4d, #6, #7, #8, #10, #19a, #19b, #19c, #24a, #24b, #24c, #24d, #36 cons, #82, #83 cons, #105a, #105b, #109 cons, #111 cons, #112 cons, #115 cons). Genome diversity was investigated by use of the nucleotide sequences of a number of NLV variants, including these new variants, the prototype (standard strain; M87661 Norwalk), and known NLV (GI) variants which had already been registered in Genbank (L07418/Southampton, L23828-2KY-89/89/J, U04469-2/DSV395, AF093797 BS5, 95/Malta, Musgrove/89/UK, Thistlehall/90/UK, Winchester/94/UK, Sindlesham/95/UK, Whiterose/96/UK, Birmingham/93/UK), and the most highly conserved gene region was searched.

In the present invention, the reference employed as a basis for describing a gene region is the nucleotide sequence (cDNA sequence) of a gene of the above-mentioned prototype (standard strain), M87661 Norwalk. FIG. 1 shows the results of the investigation of genome diversity. In chart i) of FIG. 1, the X-axis represents the base number—as counted from the 5'-terminus—of the gene (cDNA) of the above-mentioned prototype of NVLs (GI), and the Y-axis represents the degree of conservation (the greater the Y-axis value, the more analogous the nucleotide sequences of respective strains, meaning that the gene is highly conserved, and conversely, the smaller the Y-axis value, the more varied the nucleotide sequences of respective strains, meaning that the gene is less conserved). Chart ii) of FIG. 1 shows functions, in NLVs (GI), of the gene having the above-described nucleotide sequence.

Analysis of the genes of NLVs (GI) shown in FIG. 1 revealed that the region in which the genes from respective strains exhibit the highest homology lies between the vicinity of the C-terminus of the ORF1 region and the vicinity of the N-terminus of the ORF2 region, where the maximum value of homology was found to be 90% or more.

Figure 2A:
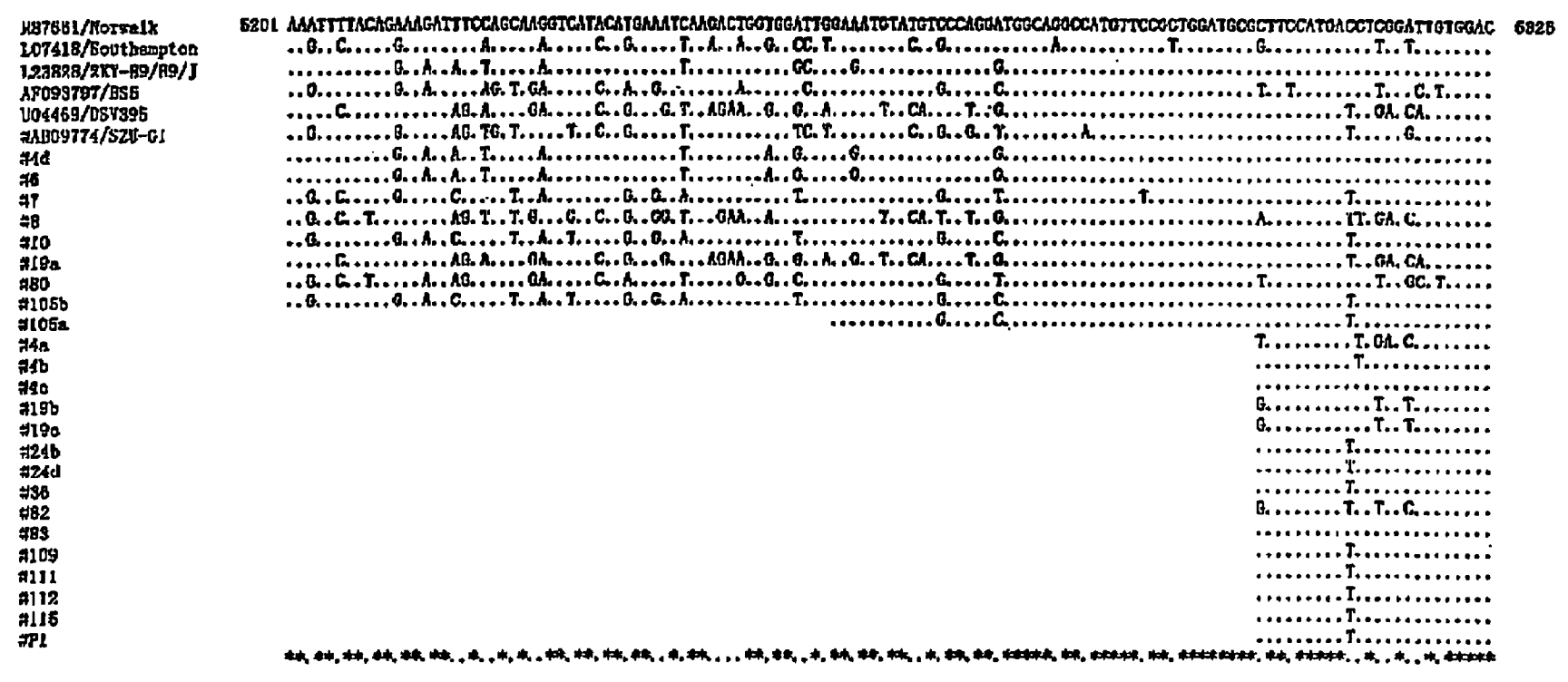
Figure 2B:
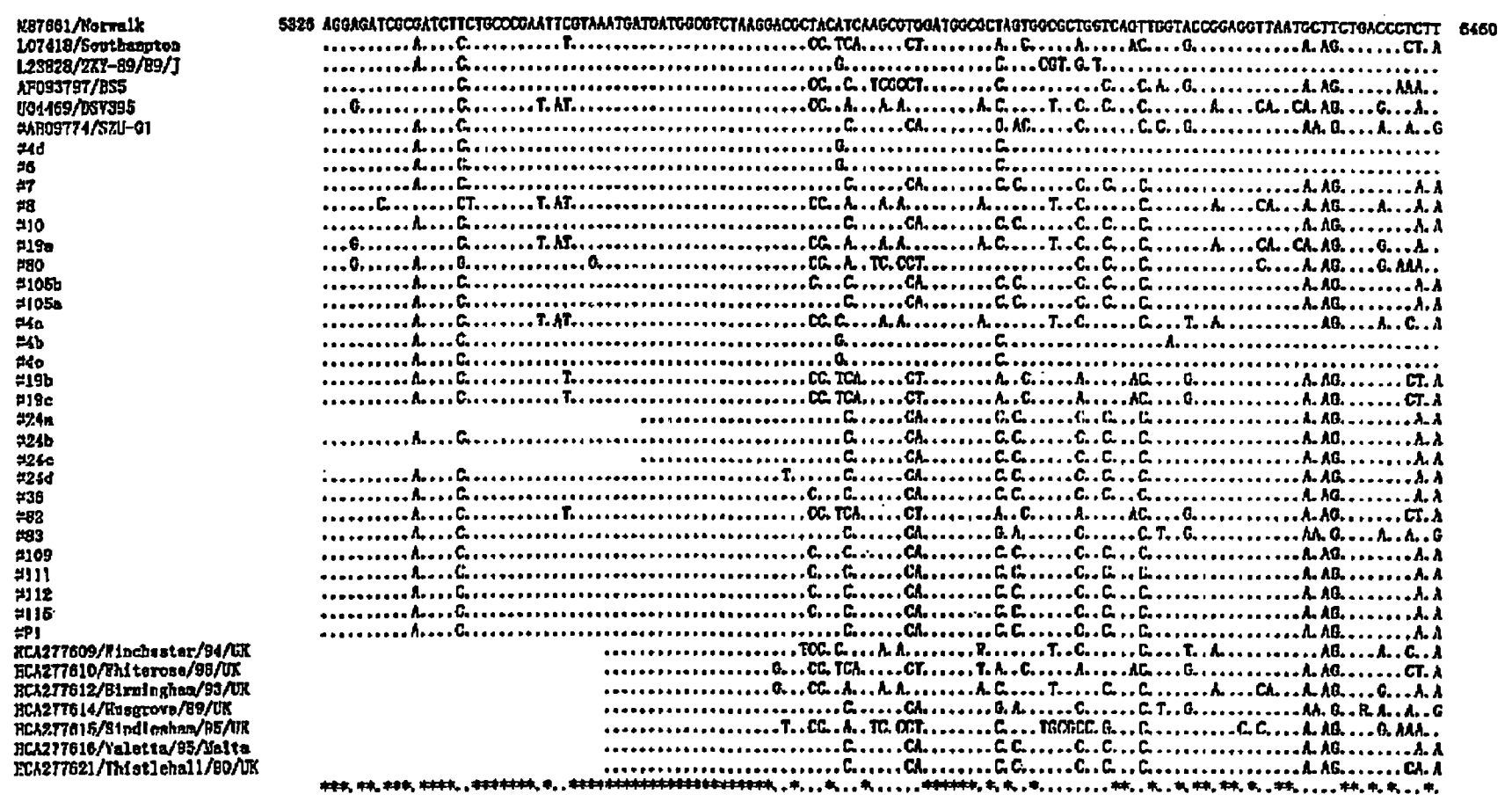
Figure 2C:
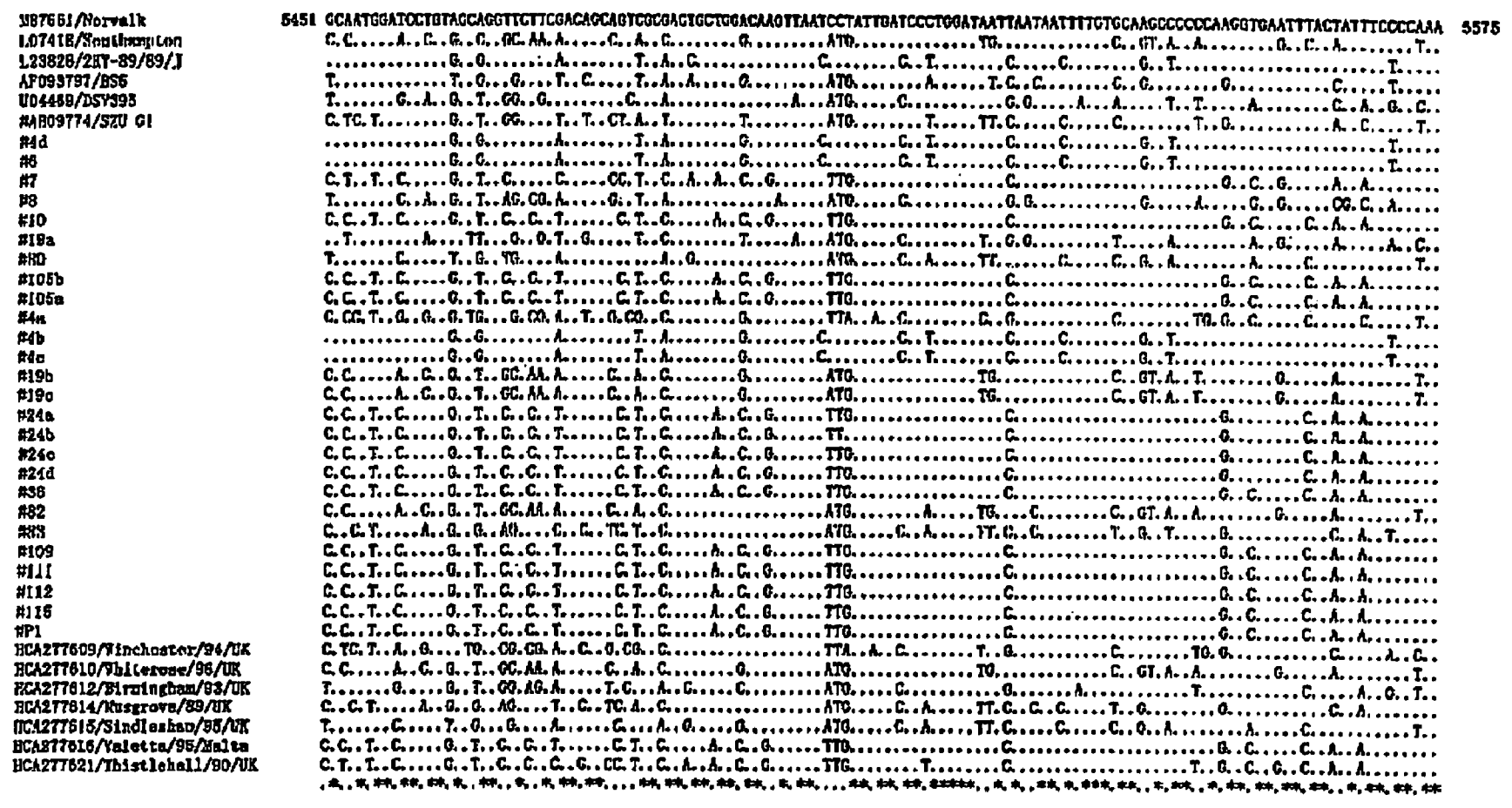
Figure 2D:
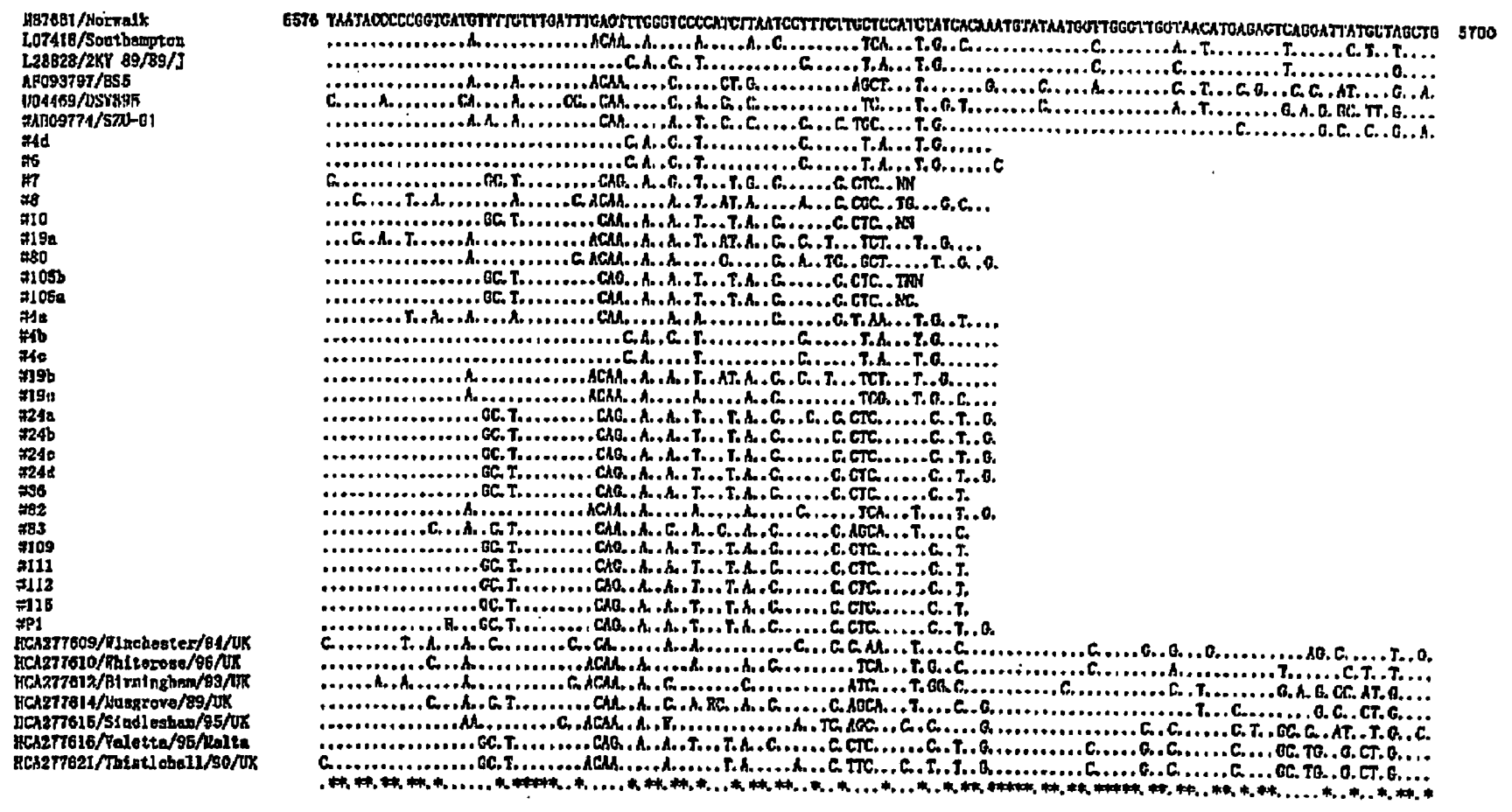

FIGS. 2A to 2D show, in an orderly arranged form for the purpose of comparison, nucleotide sequences of the respective strains of NLVs (GI), spanning from the vicinity of the C-terminus of ORF1 (FIG. 2A) to the vicinity of the N-terminus of ORF2 (FIGS. 2C and 2D; Note that FIG. 2B shows nucleotide sequences of a region that bridges ORF1 and ORF2). In FIGS. 2A to 2D, the names of the respective strains of NLVs (GI) employed are shown in the left column, and the nucleotide sequence of the prototype (standard strain) is shown in the uppermost row. As described hereinabove, in the present invention, the base number of the prototype shown in the uppermost row is employed as a reference. In the nucleotide sequences of respective strains (excepting the prototype), the symbol "." represents that the base at that position is the same as that of the prototype (standard strain), and the vacancies indicate that the bases found at the corresponding positions in the prototype are absent. The symbol "★" in the lowermost row indicates that the base at that position is in common throughout the strains, and the symbol "." in the lowermost row indicates the presence of any difference in base among the strains.

(3) Conclusion

The investigation on gene conservation of NLVs (GI) has clarified that the nucleotide sequences region exhibiting gene conservation of such a degree that enables use of that region in detection of NLVs (GI) is a region corresponding to the 5201- to 5700-positions of the nucleotide sequence of the cDNA of the prototype (standard strain) of NLVs (GI) and that, notably, a region corresponding to the 5273- to 5446-positions of the nucleotide sequence is highly conserved. [Within this context, the expression "corresponding to" is used to describe a relation between two corresponding nucleotide sequence regions, one being from the cDNA of the above-mentioned prototype and the other being from a variant, which relation is elucidated through gene analysis of NLVs (GI), including variants. Specific examples include nucleotide sequences of NLVs (GI) shown in FIGS. 2A to 2D, which correspond to the gene region represented by the above-mentioned nucleotide sequence of the cDNA of the prototype.]

The present invention is directed to means for rapidly and accurately detecting NLVs (GI) by making use of the nucleotide sequence of a nucleic acid in a highly conserved gene region (i.e, the region corresponding to the 5201- to 5700-positions of the nucleotide sequence of the cDNA of the prototype (standard strain) of NLVs (GI), hereinafter such a gene region is also referred to as a "conserved region"), which is determined through gene analysis regarding gene conservation of NLVs (GI). Specifically, the present invention provides a viral detection method for Norwalk-like viruses (GI) in a specimen (hereinafter also referred to as "the present detection method") by use of, as an index, the nucleic acid fragment of a complementary nucleotide sequence or complementary nucleotide sequences (hereinafter collectively called "a complementary nucleotide sequence") corresponding to the 5201- to 5700-positions (preferably 5276- to 5446-positions, more preferably 5276- to 5380-positions and/or 5319- to 5446-positions) of the nucleotide sequence of the cDNA of the prototype (standard strain) of NLVs (GI).

As used herein, the word "complementary" is used to describe a relation where a nucleic acid fragment having a certain nucleotide sequence exhibits such a degree of complementation that enables hybridization with another nucleic acid fragment under stringent conditions (56 to 68° C., in the presence of 50 mM or more sodium ions), and the expression "complementary nucleotide sequence" encompasses the following incidences: The "complementary nucleotide sequence" is minus-stranded with respect to a plus-stranded fragment of the nucleotide sequence; the "complementary nucleotide sequence" is plus-stranded with respect to a minus-stranded fragment of the nucleotide sequence; and one "complementary nucleotide sequence" is minus-stranded with respect to a plus-stranded fragment of the nucleotide sequence and the other "complementary nucleotide sequence" is plus-stranded with respect to a minus-stranded fragment of the nucleotide sequence.

BRIEF DESCRIPTION OF THE DRAWINGS

FIG. 2A shows nucleotide sequences identified in respective strains of NLVs (GI), arranged for facilitating comparison, the sequences coding for the vicinity of the C-terminus of the ORF1 region. FIG. 2A shows the following nucleotide sequences. ordered from top to bottom in the figure: nucleotides 1–125 of SEQ ID NO:16–29: nucleotides 1–68 of SEQ ID NO:30: nucleotides 1–24 of SEQ ID NOs:31, 32, 33, 34, 35, 37, 39, 40, 41, 42, 43, 44, 45, 46, and 47.

FIG. 2B shows nucleotide sequences identified in respective strains of NLVs (GI), arranged for facilitating comparison, the sequences coding for the region from the vicinity of the C-terminus of the ORF1 region to the vicinity of the N-terminus of the ORF2 region. FIG. 2B shows the following nucleotide sequences, ordered from top to bottom in the figure: nucleotides 126–250 of SEQ ID NOs:16–29; nucleotides 69–193 of SEQ ID NO:30; nucleotides 25–149 of SEQ ID NOs:31–35; nucleotides 1–89 of SEQ ID NO:36; nucleotides 25–149 of SEQ ID NO:37; nucleotides 1–89 of SEQ ID NO:38; nucleotides 25–149 of SEQ ID NOs:39–47; nucleotides 1–93 of SEQ ID NOs:48–54.

FIG. 2C shows nucleotide sequences identified in respective strains of NLVs (GI), arranged for facilitating comparison, the sequences coding for the vicinity of the N-terminus of the ORF2 region (part 1 of 2). FIG. 2C shows the following nucleotide sequences, ordered from top to bottom in the figure: nucleotides 251–375 of SEQ ID NOs:16–29; nucleotides 194–318 of SEQ ID NO:30; nucleotides 150–274 of SEQ ID NOs:31–35; nucleotides 90–214 of SEQ ID NO:36; nucleotides 150–274 of SEQ ID NO:37; nucleotides 90–214 of SEQ ID NO:38; nucleotides 150–274 of SEQ ID NOs:39–47; nucleotides 94–218 of SEQ ID NOs:48–54.

FIG. 2D shows nucleotide sequences identified in respective strains of NLVs (GI), arranged for facilitating comparison, the sequences coding for the vicinity of the N-terminus of the ORF2 region (part 2 of 2). FIG. 2D shows the following nucleotide sequences, ordered from top to bottom in the figure: nucleotides 376–500 of SEQ ID NOs:16–21; nucleotides 376–451 of SEQ ID NO:22; nucleotides 376–452 of SEQ ID NO:23; nucleotides 376–442 of SEQ ID NO:24; nucleotides 376–45 1 of SEQ ID NO:25; nucleotides 376–442 of SEQ ID NO:26; nucleotides 376–450 of SEQ ID NO:27; nucleotides 376–452 of SEQ ID NO:28; nucleotides 376–443 of SEQ ID NO:29; nucleotides 319–386 of SEQ ID NO:30; nucleotides 275–351 of SEQ ID NOs:31–35; nucleotides 215–291 of SEQ ID NO:36; nucleotides 275–351 of SEQ ID NO:37; nucleotides 215–291 of SEQ ID NO:38; nucleotides 275–351 of SEQ ID NO:39; nucleotides 275–348 of SEQ ID NO:40; nucleotides 275–351 of SEQ ID NO:41; nucleotides 275–348 of SEQ ID NOs:42–46; nucleotides 275–351 of SEQ ID NO:47; nucleotides 219–343 of SEQ ID NOs:48–54.

BEST MODE FOR CARRYING OUT THE INVENTION

Figure 1:
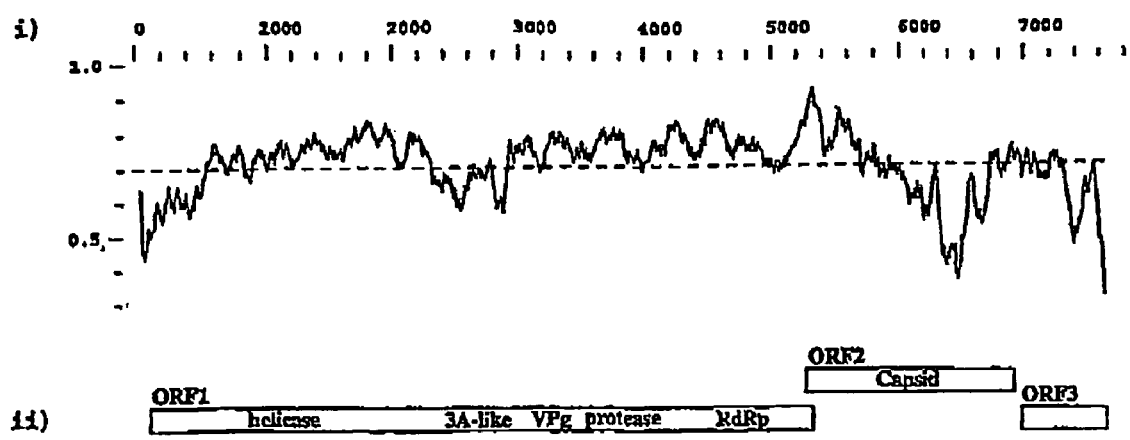
FIG. 1 shows the results of the investigation of genome diversity of NLVs (GI).

Modes for carrying out the present invention will next be described.

In order to make use of the finding on conserved regions of NLVs (GI) as an index for detecting NLVs (GI), the conserved regions must be amplified through a nucleic acid amplification method, to thereby produce gene amplification products of the conserved regions. Examples of such an amplification method include PCR and other methods, such as RT-PCR, NASBA (nucleic acid sequence based amplification), and SDA (strand displacement amplification). In any of these methods, gene amplification primers must be designed and prepared so as to be adapted to the method. Generally, gene amplification primers are designed such that a gene region is amplified in both directions of forward (5'→3') and reverse, with the gene region being sandwiched by +/− primers. Since the gene amplification primers must properly bind to the intended regions of the gene serving as a template for attaining complementary binding, it is necessary that any of such primers contain at least a minimum number of bases forming a nucleotide sequence complementary only to characteristic nucleotide sequence(s). Such a gene amplification primer has at least 10 bases, preferably about 15 to 30 bases. In addition, for 5 bases counted from the 3'-terminus in a region that is to achieve a complementary binding, the primer is preferably designed to be as precisely complementary as possible.

Moreover, the gene region which is employed as a basis for establishing gene amplification primers must at least meet the requirement that the resultant gene amplification product contains a complementary nucleotide sequence corresponding to a conserved region or a highly conserved region (which will be described hereinbelow). From this viewpoint, a preferred gene amplification primer comprises a complementary nucleotide sequence corresponding to consecutive 10 or more bases, preferably consecutive 15 to 30 bases, of a nucleotide sequence selected, as a benchmark, from the group consisting of nucleotide sequences of the 5276- to 5310-positions of the nucleotide sequence of the cDNA of the prototype (standard strain) of NLVs (GI), the 5319- to 5349-positions thereof, the 5354- to 5380-positions thereof, and the 5426- to 5446-positions thereof.

Nucleic acids having nucleotide sequences that correspond to a conserved region—the nucleic acids serving as indices in detection of NLVs (GI) in the present invention—are obtained as follows: at least two nucleotide sequences having 10 or more consecutive bases (preferably a complementary nucleotide sequence having 15 to 30 bases) are selected from the conserved region; and through use of gene amplification primers established on the basis of the selected nucleotide sequences, genes obtained from specimens are subjected to the above-mentioned amplification means, to thereby yield the target nucleic acids as the gene amplification products. Preferably, the gene amplification products include a region corresponding to the 5276- to 5446-positions of the nucleotide sequence of the cDNA of the prototype of NLVs (GI), which is a considerably highly conserved region within the aforementioned conserved regions (hereinafter may be referred to as a "highly conserved region"). More preferably, the nucleotide sequence to be included in the gene amplification products obtained from the highly conserved region is a segment or segments corresponding to the 5276- to 5380-positions and/or the 5319- to 5446-positions of the complementary nucleotide sequence of the cDNA of the prototype of NLVs (GI).

Notably, within the highly conserved region of the genes of NLVs (GI), a nucleotide sequence corresponding to the 5319- to 5380-positions of the nucleotide sequence of the cDNA of the prototype (standard strain) of NLVs (GI) are more highly conserved (hereinafter this region may be referred to as a "very highly conserved region"), and nucleotide sequences corresponding to the 5319- to 5349-positions and the 5354- to 5380-positions of the prototype's cDNA nucleotide sequence are still more highly conserved (hereinafter these regions may be referred to as "significantly highly conserved regions"). Taken the above together, nucleotide sequences based on which gene amplification primers are established preferably constitute either set <1> or <2> below, each set being formed of two nucleotide sequences which serve as standards.

<1> A set consisting of two complementary nucleotide sequences; one corresponding to the 5276- to 5310-positions and the other corresponding to the 5354- to 5380-positions of the nucleotide sequence of the cDNA of the prototype of NLVs (GI).

<2> A set consisting of two complementary nucleotide sequences; one corresponding to the 5319- to 5349-positions and the other corresponding to the 5426- to 5446-positions of the nucleotide sequence of the cDNA of the prototype of NLVs (GI).

When genes of NLVs (GI) are amplified through use of gene amplification primers of set <1>, the resultant gene amplification products will contain a nucleotide sequence corresponding to the 5319- to 5349-positions of the nucleotide sequence of the cDNA of the prototype of NLVs (GI), whereas when genes of NLVs (GI) are amplified through use of gene amplification primers of set <2>, the resultant gene amplification products will contain a nucleotide sequence corresponding to the 5354- to 5380-positions of the nucleotide sequence of the cDNA of the prototype. Therefore, through use of means which enables detection of the nucleotide sequences of the mentioned significantly highly conserved regions, most typically, through use of nucleic acid probes for detection complementary to a complementary nucleotide sequence containing a portion of or the entirety of the significantly highly conserved regions falling within the nucleic acid of the detection target, detection and quantitation of the resultant gene amplification product, which is the target of detection, can be attained, and using the quantitation/detection results as indices, NLVs (GI) can be detected rapidly and accurately.

Each of the above-described gene amplification primers may be employed as a component of the detection kit of the present invention described hereinbelow.

Notably, the present detection method can be applied to any specimen in which NLVs (GI) are to be detected. For example, when NLVs (GI) are to be detected in a food-poisoning patient, stool of the patient is typically employed as a specimen, and depending on the case, vomitus, blood, etc. may be employed. When NLVs (GI) are to be detected in food or a food production facility, the food itself, deposits collected from the food production facility, clothing of food production workers, etc. may be employed as a specimen. Moreover, the specimen may be obtained from watery sources, such as various types of sewage or discharging water, seawater, river water, and lake water. In order to obtain genes from the aforementioned specimens, suitable methods are selected according to the type of the specimen to be employed. Generally, a specimen is immersed or suspended in water or a similar medium, and from a supernatant fraction obtained therefrom, viral RNA is extracted, through a conventional method such as the acid phenol method (e.g., the acid guanidinum-phenol-chloroform (AGPC) method). The thus-obtained viral RNA is processed through a suitably selected gene amplification method. For example, through preparation of cDNA having a nucleotide sequence complementary to the nucleotide sequence of the viral RNA using a reverse transcriptase—to thereby obtain a nucleic acid sample. The nucleic acid sample is then subjected to gene amplification by use of the aforementioned gene amplification primers, whereby a gene amplification product of interest can be obtained (generally, the presence of the product of interest can be confirmed through electrophoresis on the basis of size of the target product).

As described above, NLVs (GI) can be rapidly and accurately detected by detecting, as an index of the presence of the NLVs (GI), a complementary nucleotide sequence corresponding to the conserved region, preferably to the highly conserved region, more preferably to the very highly conserved region, still more preferably to the significantly highly conserved region of the thus-obtained gene amplification product.

Conventional means may be employed to detect, as an index of the presence of NLVs (GI), a certain specific nucleotide sequence of a gene amplification product. Typically, through use of nucleic acid probes for detection (for example, nucleic acid fragments which have been labeled with a fluorophore or a radioisotope) containing nucleotide sequences complementary to the aforementioned complementary nucleotide sequence(s) that serve(s) as an index of virus detection, the presence or absence of the nucleotide sequence of the gene amplification product can be confirmed by hybridization or a similar method (as a negative result or positive result). Generally, such detection means is performed on the amplification product after the gene amplification process has completed. However, such a procedure involves a drawback in that since a technician must open a tube to remove the analytical sample after gene amplification reaction, there will be increased chances where experimental facilities or reagents may be polluted with the gene amplification product, and in addition, extra time and labor may be required. Moreover, the polluting gene amplification product may invite the risk of false positive results, raising critical problems in the field of detection. Accordingly, in order to avoid risks such as pollution and to minimize the time required for detection, it is recommended to use, during gene amplification, means enabling monitoring of the presence of a specific nucleotide sequence of the gene amplification product. Examples of typical methods employing such means include, but are not limited to, 1) a detection method by use of a molecular beacon probe, and 2) a detection method by use of a Taq-Man probe.

1) The detection method by use of a molecular beacon probe makes use of a hair-pin shaped hybridization probe (molecular beacon probe) for allowing fluorescent monitoring of a gene amplification product obtained by PCR during or after an amplification procedure (Nature Biotechnology, 1998, 16: 49–53). Terminal sequences of the nucleic acid fragment constituting the molecular beacon probe are complementary to each other. Typically, the terminal portions are bonded to each other, whereby a "stem-loop structure" is formed. The loop portion of the stem-loop structure is designed so as to be complementary to a region of interest (i.e., a conserved region, a highly conserved region, a very highly conserved region, or a significantly highly conserved region: hereinafter, such regions may be collectively referred to as a "Conserved Region") of the gene amplification product. Moreover, to one end of the nucleic acid of the probe, a fluorophore is bound, and to the other end of the nucleic acid of the probe, a non-fluorescent quencher dye is bound. When the probe is present in a solution in a free state, the probe has a hairpin structure, whereby the fluorophore and the quencher interact each other, and fluorescence is not detected. However, when the solution contains the gene amplification product having a nucleotide sequence complementary to the nucleotide sequence of the probe, the loop portion is bound to the complementary nucleotide sequence portion. As a result, the overall structure of the probe varies, resulting in a separation of the fluorophore and the quencher from each other, and thus quenching effect of the quencher for the fluorophore is canceled. Therefore, fluorescence emitted from the fluorophore can be observed. Increase in fluorescence intensity caused by canceling of the quenching effect is proportional to the increment in the amount of the gene amplification product having the nucleotide sequence complementary to the sequence of the nucleic acid that forms the probe. Through monitoring the increase in the fluorescence intensity, the presence of the target nucleotide sequences (e.g., sequences of Conserved Regions of NLVs (GI)) can be detected not only after completion of gene amplification, but also during gene amplification. That is, NLVs (GI) in a specimen can be detected through use of the results of the aforementioned increase in fluorescence intensity as an index.

Labeling of a molecular beacon probe through use of the aforementioned fluorophore and the quencher is typically performed as follows. The 5'-terminus of the nucleic acid probe is labeled with a fluorescein fluorophore (such as 6-carboxyfluorescein (6-FAM) or 6-carboxy-4,7,2',7'-tetrachlorofluorescein (TET)) or a rhodamine fluorophore (such as 5-carboxytetramethylrhodamine (TAMARA)), and the 3'-terminus of the probe is labeled with a quencher (such as 4-(4'-dimethylaminophenylazo)benzoic acid (DABCYL)) (see, for example, Nature Biotechnology, 1996, 14: 303–308).

2) The detection method by use of a Taq-Man probe makes use of a hybridization probe (Taq-Man probe) for allowing fluorescent monitoring of a gene amplification product obtained by PCR during the amplification procedure (see, for example, Experimental Medicine, Vol. 15, No. 7 (extra issue), pp. 46–51, 1997). The Taq-Man probe is a nucleic acid fragment bearing a fluorescein fluorophore label (reporter dye) and a rhodamine fluorophore label (quencher dye) at the 5'-terminus and 3'-terminus of the fragment, respectively. When the reporter dye and the quencher dye are linked to each other via the nucleic acid fragment, due to Forster resonance energy, the quencher dye inhibits fluorescence emission of the reporter dye. However, as elongation proceeds along with the progress of annealing of a nucleic acid (in the gene amplification product) which is complementary to the nucleic acid of the Taq-Man probe performed through use of primers and the Taq-Man probe, hydrolysis occurs from the 5'-terminus of the Taq-Man probe under 5'→3' endonuclease activity of Taq DNA polymerase. As a result, the 5'-terminal reporter dye is released from the 3'-terminal quencher dye, resulting in an increase in fluorescence intensity of the reporter dye which has been suppressed. The increase in fluorescence intensity caused by the reporter dye is proportional to the increase in the amount of the gene amplification product having the nucleotide sequence complementary to the sequence of the nucleic acid that forms the probe. Through monitoring the increase in fluorescence intensity, the presence of the nucleotide sequence of interest (e.g., Conserved Regions of NLVs (GI)) can be detected not only after completion of gene amplification, but also during gene amplification. Thus, NLVs (GI) in a detection specimen can be detected through use of the results of the aforementioned increase in fluorescence intensity as an index.

Labeling of a Taq-Man probe with the aforementioned fluorophore is typically performed in accordance with a conventional method by labeling the 5'-terminus of the probe with a fluorescein fluorophore (such as 6-FAM or TET), and the 3'-terminus of the probe with a rhodamine fluorophore (such as TAMARA) (see, for example, Nucleic Acids Research, 1993, 21 (16): 3761–3776).

All the aforementioned nucleic acid probes to be used for detection purposes (hereinafter also referred to as nucleic acid probes for detection) may be employed as components of the detection kit of the present invention which will be described below.

In relation to the detection of NLVs (GI) according to the present detection method, detection of a gene amplification product or a similar product having a nucleotide sequence of interest may be performed by way of quantitation of the nucleic acid fragment of interest through use of the aforementioned means. Alternatively, instead of quantitation, NLVs (GI) may be detected in the form of qualitative (e.g., positive or negative) information. By use of the detection results of the gene amplification products (quantitative value or qualitative information) as an index, and by correlating the index to the presence/absence or the amounts of the NLVs (GI) in the specimen, the NLVs (GI) of interest can be detected.

The present invention also provides a kit for detecting NLVs (GI) (hereinafter, the kit will be referred to as the present detection kit) for performing the present detection method.

The present detection kit typically contains primers for amplifying—by RT-PCR or any other suitable method—a nucleic acid fragment having any of Conserved Regions of NLVs (GI), and/or one or more probes for detecting the Conserved Regions of a gene amplification product. Preferably, the kit contains both; primers and probes.

The gene amplification primers are nucleic acid fragments capable of producing gene amplification products through amplification of a Conserved Region of an NLV (GI) gene by use of gene amplification means such as RT-PCR. The nucleic acid probes for detection contain nucleic acid fragments having nucleotide sequences complementary to sequences corresponding to the nucleotide sequences of a Conserved Region. As described above, one may employ nucleic acid probes for detection of a basic mode comprising complementary nucleotide sequences labeled with a fluorophore or a radioisotope. In particular, when NLVs (GI) are detected in the course of gene amplification, preferably, there may be employed such nucleic acid probes for detection produced by incorporating nucleic acids of a complementary nucleotide sequence into the aforementioned molecular beacon probe or Taq-Man probe.

Details of the gene amplification primers and the nucleic acid probes for detection which may be included in the present detection kit have already been described in relation to the present detection method. Specific examples of such primers and probes are also described in the Example section below.

EXAMPLE

The present invention will next be described by way of example, which should not be construed as limiting the technical scope of the invention.

[Preparation of Primers and Probes]

Detection of NLVs (GI) in the present example was performed by use of the following nucleic acid primers for gene amplification and nucleic acid probes for gene detection. The nucleic acids described below were chemically synthesized by use of a full-automated ABI 3948 Nucleic Acid Synthesis and Purification System (Applied Biosystems).

Gene Amplification Primers

[Forward Primers]

Set A (mixed):
    5' ATCGCRATCTYCTGCCCG 3' (SEQ ID NO: 1, corresponding to the 5331- to 5348-positions of the nucleotide sequence of the prototype)
    5' ACCGCRATCTYTTGCCCG 3' (SEQ ID NO: 2, corresponding to the 5331- to 5348-positions of the nucleotide sequence of the prototype)

Set B (mixed):
    5' CGYTGGATGCGNTTCCATGA 3' (SEQ ID NO: 3, corresponding to the 5291- to 5310-positions of the nucleotide sequence of the prototype)
    5' CGYTGGATGCGNTTTCATGA 3' (SEQ ID NO: 4, corresponding to the 5291- to 5310-positions of the nucleotide sequence of the prototype)

Set C (mixed):
    5' CGYTGGATGCGNTTCCATGA 3' (SEQ ID NO: 3, corresponding to the 5291- to 5310-positions of the nucleotide sequence of the prototype)
    5' CGYTGGATGCGNTTTCATGA 3' (SEQ ID NO: 4, corresponding to the 5291- to 5310-positions of the nucleotide sequence of the prototype)

[Reverse Primers]

Set A (mixed):
    5' GGBTCAGCTGTRTTTGCCTCTG 3' (SEQ ID NO: 5, corresponding to a nucleotide sequence that is complementary to the 5425- to 5446-positions of the nucleotide sequence of the prototype)
    5' GGBTCAGAAGCATTAACCTCCG 3' (SEQ ID NO: 6, corresponding to a nucleotide sequence that is complementary to the 5425- to 5446-positions of the nucleotide sequence of the prototype)
    5' GGBTCAGCTGTRTTAACCTCCG 3' (SEQ ID NO: 7, corresponding to a nucleotide sequence that is complementary to the 5425- to 5446-positions of the nucleotide sequence of the prototype)
    5' GGBTCAGCATTRTTAACCTCCG 3' (SEQ ID NO: 8, corresponding to a nucleotide sequence that is complementary to the 5425- to 5446-positions of the nucleotide sequence of the prototype)

Set B:
    5' CTTAGACGCCATCATCATTYAC 3' (SEQ ID NO: 9, corresponding to a nucleotide sequence that is complementary to the 5354- to 5375-positions of the nucleotide sequence of the prototype)

Set C:
    5' TCCTTAGACGCCATCATCATT 3' (SEQ ID NO; 10, corresponding to a nucleotide sequence that is complementary to the 5357- to 5377-positions of the nucleotide sequence of the prototype)

Nucleic Acid Probes for Gene Detection

[Taq-Man Probes]

Set A:
    5' TAAATGATGATGGCGTCTAAGGACGC 3' (SEQ ID NO: 11, corresponding to a nucleotide sequence that is complementary to the 5355- to 5380-positions of the nucleotide sequence of the prototype)

Set B:
    5' TCGGGCAGGAGATYGCG 3' (SEQ ID NO: 12, corresponding to a nucleotide sequence that is complementary to the 5333- to 5349-positions of the nucleotide sequence of the prototype)

Set C (mixed):
    5' AGATYGCGATCYCCTGTCCA 3' (SEQ ID NO: 13, corresponding to a nucleotide sequence that is complementary to the 5320- to 5340-positions of the nucleotide sequence of the prototype)
    5' AGATCGCGGTCTCCTGTCCA 3' (SEQ ID NO: 14, corresponding to a nucleotide sequence that is complementary to the 5320- to 5340-positions of the nucleotide sequence of the prototype)

The 5'-terminus and the 3'-terminus of all the Taq-Man probes used in the present example were labeled with TET and TAMARA, respectively (labeling was performed in accordance with the method described in Nucleic Acids Research (1993, 21 (16): 3761–3766)).

[Molecular Beacon Probes (the Lowercase Letters Denote Stem Portions)]

Set A:
    5' ccgtcgTAAATGATGATGGCGTCTAAGGACcgacgg 3' (SEQ ID NO: 15, Uppercase letters correspond to the 5355- to 5378-positions of the nucleotide sequence of the prototype)

Set B:
    5' ccgctgTCGGGCAGGAGATYGCGcagcgg 3' (SEQ ID NO:55, Uppercase letters correspond to a nucleotide sequence that is complementary to the 5333- to 5349-positions of the nucleotide sequence of the prototype)

Set C (mixed):

5' ccgctgAGATYGCGATCYCCTGTCCAcagcgg 3' (SEQ ID NO:56, Uppercase letters correspond to a nucleotide sequence that is complementary to the 5320- to 5340-positions of the nucleotide sequence of the prototype)

5' ccgctgAGATCGCGGTCTCCTGTCCAcagcgg 3' (SEQ ID NO:57, Uppercase letters correspond to a nucleotide sequence that is complementary to the 5320- to 5340-positions of the nucleotide sequence of the prototype)

The 5'-terminus and the 3'-terminus of all the molecular beacon probes used in the present example were labeled with TET and DABCYL, respectively (labeling was performed in accordance with the method described in Nature Biotechnology (1996, 14: 303–308)).

Nucleic acids having nucleotide sequences complementary (in a strict sense) to the nucleotide sequences of the above-described nucleic acid probes were chemically synthesized, and the resultant nucleic acids were used together with the gene detection probes.

[Detection of Virus]

(1) The detection method of the present invention was performed on the RNA samples extracted from stool specimens collected from 44 cases of non-bacterial gastroenteritis from which NLV particles were detected through electron microscopy performed in the Saitama Institute of Public Health during the period from 1998 to 2000, the specimens being the same as those employed in the above-described test to investigate highly conserved regions of NLV (GI) genes.

First, each of the RNA samples was subjected to reverse transcription reaction. Briefly, each of the RNA samples (8 μL) was mixed with a 12 μL solution for reverse transcription reaction. (The solution was prepared as follows: A dNTP solution (10 mM, 1 μL), random hexamer (75 pmol), RNasin (30 units Promega, USA), SuperScript II RNaseH (−) Reverse Transcriptase (200 units, Gibco BRL, USA), DTT (100 mM, 1 μL), and a 5-fold diluted reverse transcription buffer (250 mM, Tris-HCl (pH 8.3), 275 mM KCl, 15 mM $MgCl_2$) were mixed, and the mixture was diluted with sterilized distilled water to attain a total volume of 12 μL). The mixture was allowed to react at 42° C. for one hour or more. Subsequently, the resultant mixture was subjected to enzyme inactivation reaction for 15 minutes at 70° C., whereby a cDNA sample corresponding to each of the RNA samples (RT products) was prepared. Separately, a reaction mixture was prepared as follows: A buffer (25 μL), RT products (5 μL), primer (50 nM each), and fluorescent probe (Taq-Man probe, 5–20 pmol) were mixed, and the mixture was diluted with sterilized distilled water to attain a total volume of 50 μL (the Taq-Man probe of Set A was used for a system including the Set A gene amplification primers; the Taq-Man probe of Set B was used for a system including the Set B gene amplification primers; and the Taq-Man probes of Set C were used for a system including the Set C gene amplification primers). The reaction mixture was subjected to PCR reaction by use of the nucleic acid fragment of the aforementioned Set A, Set B, or Set C as a primer set for gene amplification, and a Taq-Man universal buffer Kit (ABI, USA) (PCR cycle: 50° C. for two minutes→95° C. for 10 minutes→(95° C. for 1 minute→56° C. for three minutes)×50 cycles)). The fluorescence intensity was monitored over time during the reaction by use of AB17700 (ABI, USA).

A cDNA fragment of SzuGI strain was subjected to cloning by use of pT7blue vector (Novagen, USA) through a conventional method. The fragment has a nucleotide sequence corresponding to the 5207- to 5696-positions of the nucleotide sequence of the cDNA of the prototype (standard strain) of NLVs (GI). Through use of the thus-cloned cDNA as a positive control specific to NLVs (GI), NLV (GI) gene detection was performed in accordance with the aforementioned procedure. In all the cases in which the primers and probes of Set A, B, or C were used, the following were confirmed: $10^1$ to $10^7$ copy genes of NLVs (GI) can be detected (detection limit: $10^1$ copy genes/reaction), and NLVs (GI) can be quantitatively detected by reference to Ct values (threshold cycle number).

Among the aforementioned stool specimens which had been collected from 44 patients of non-bacterial gastroenteritis, 16 cases (36.4%) were found to be NLV (GI) positive, whereas the remaining 28 cases (63.6%) were found to be NLV (GI) negative. However, in all these 28 cases, NLVs (GII) were detected by another method. Taking the results regarding these two types of NLVs (GI and GII) together, the detection rate of NLVs was found to be 100%.

In cases using a system similar to the above and also using molecular beacon probes A, B, or C (corresponding to gene amplification primers of Set A, B, or C), results similar to those described above were obtained.

(2) In order to demonstrate that the detection method of the present invention can be carried out on food, the method was performed through use of fresh oysters instead of the aforementioned stool specimens as test specimens.

From each of the 40 fresh oyster individuals, the midgut gland was removed, and sterilized distilled water was added thereto. Subsequently, the midgut gland was subjected to three cycles of freezing and thawing, whereby the tissues of the midgut gland were lyzed. The lyzed tissues were subjected to centrifugation at 10,000×g for 20 minutes. Prom the supernatant (140 μL) obtained through the centrifugation, nucleic acid was extracted through use of QIA Viral RNA (QIAGEN, USA) in accordance with the manufacturer's protocol. The extract was suspended in sterilized distilled water (50 μL). Through use of the suspension as an RNA sample of each fresh oyster, the detection method of the present invention was carried out by use of a molecular beacon probe set (Set B) in accordance with the procedure described in (1) above (gene amplification primers employed were those of Set B).

As a result, NLVs (GI) were detected in three fresh oyster individuals.

The results obtained in (1) and (2) clarified that the detection method of the present invention enables rapid, accurate detection of NLVs (GI). Moreover, as described above, through use of a nucleic acid probe specific to NLVs (GI) as a primer for gene detection, by monitoring the gene amplification process, the detection method of the present invention enables quantitative detection of NLVs (GI). In conclusion, the present invention provides a virus detection method of very high sensitivity and efficiency.

INDUSTRIAL APPLICABILITY

The present invention has identified a highly conserved gene region in the genes of NLVs (GI), and on the basis of this finding, a rapid, accurate means for detecting NLVs is provided.

The invention claimed is:

1. A method of detecting a Norwalk-like virus (GI) in a sample comprising:
   (a) performing a nucleic acid amplification reaction on a sample using at least two oligonucleotide primers, wherein each oligonucleotide primer comprises a nucleotide sequence complementary to a region of at least 10 consecutive nucleotides of positons 76 to 246 of the polynucleotide sequence set forth in SEQ ID NO:16, and
   (b) detecting an amplification product, thereby detecting a Norwalk-like virus (GI) in a sample.

2. The method according to claim 1, wherein each of said oligonucleotide primers is complementary to a region of between 15 and 30 consecutive nucleotides of positions 76 to 246 of SEQ ID NO:16.

3. The method according to claim 1, wherein each of said oligonucleotide primers is independently complementary to a region of at least 10 consecutive nucleotides of SEQ ID NO:16, said region selected from the group consisting of positions 76 to 110, positions 119 to 149, positions 154 to 180, and positions 225 to 246 of SEQ ID NO:16.

4. The method according to claim 1, wherein said oligonucleotide primers are oligonucleotide primers of group (a) or group (b):
   (a) an oligonucleotide primer complementary to a region of at least 10 consecutive nucleotides of positions 76 to 110 of SEQ ID NO:16, and an oligonucleotide primer complementary to a region of at least 10 consecutive nucleotides of positions 154 to 180 of SEQ ID NO:16; and
   (b) an oligonucleotide primer complementary to a region of at least 10 consecutive nucleotides of positions 119 to 149 of SEQ ID NO:16, and an oligonucleotide primer complementary to a region of at least 10 consecutive nucleotides of positions 225 to 246 of SEQ ID NO:16.

5. The method according to claim 1, wherein said oligonucleotide primers are oligonucleotide primers of group (a), group (b) or group (c):
   (a) an oligonucleotide primer of SEQ ID NO: 1 and/or 2, and one or more oligonucleotide primers selected from the group consisting of SEQ ID NOs: 5, 6, 7, and 8;
   (b) an oligonucleotide primer of SEQ ID NO: 3 and/or 4, and the oligonucleotide primer of SEQ ID NO: 9; and
   (c) an oligonucleotide primer of SEQ ID NO: 3 and/or 4, and the oligonucleotide primer of SEQ ID NO: 10.

6. The method according to claim 1, wherein said amplification product comprises a polynucleotide sequence complementary to positions 76 to 246 of SEQ ID NO:16.

7. The method according to claim 4, wherein said amplification product comprises a polynucleotide sequence complementary to positions 76 to 180 of SEQ ID NO:16 or positions 119 to 246 of SEQ ID NO:16.

8. The method according to claim 1 wherein said detecting an amplification product is performed using an oligonucleotide probe, said probe comprising a nucleotide sequence complementary to the amplification product.

9. The method according to claim 8, wherein said oligonucleotide probe is selected from the group consisting of SEQ ID NOs:11, 12, 13, 14, 15, 55, 56 and 57.

10. The method according to claim 8, wherein the oligonucleotide probe is a molecular beacon probe or a Taq-Man probe.

11. A method of detecting a Norwalk-like virus (GI) in a sample comprising:
   (a) performing a nucleic acid amplification reaction on a sample to obtain an amplification product, said amplification product comprising a polynucleotide sequence complementary to positions 76 to 246 of SEQ ID NO: 16, and (b) detecting the amplification product using an oligonucleotide probe, said oligonucleotide probe comprising a polynucleotide sequence complementary to the amplification product.

12. The method according to claim 11, wherein said amplification product comprises a polynucleotide sequence complementary to positions 76 to 180 or positions 119 to 246 of SEQ ID NO: 16.

13. The method according to claim 11, wherein said amplification product comprises a polynucleotide sequence complementary to positions 119 to 180 of SEQ ID NO: 16.

14. The method according to claim 11, wherein said amplification product comprises a polynucleotide sequence complementary to positions 119 to 149 or positions 154 to 180 of SEQ ID NO: 16.

15. The method according to claim 11, wherein said oligonucleotide probe is selected from the group consisting of SEQ ID NOs: 11, 12, 13, 14, 15, 55, 56 and 57.

16. The method according to claim 11, wherein said oligonucleotide probe is a molecular beacon probe or a Taq-Man probe.

17. The method according to claim 11, wherein said nucleic acid amplification reaction is performed using at least two oligonucleotide primers, wherein each oligonucleotide primer comprises a nucleotide sequence complementary to a region of at least 10 consecutive nucleotides of positions 76 to 246 of SEQ ID NO: 16.

18. The method according to claim 17, wherein each of said oligonucleotide primers is independently complementary to a region of at least 10 consecutive nucleotides of SEQ ID NO:16, said region selected from the group consisting of positions 76 to 110, positions 119 to 149, positions 154 to 180, and positions 225 to 246 of SEQ ID NO: 16.

19. The method according to claim 17, wherein said oligonucleotide primers are oligonucleotide primers of group (a) or group (b):
  (a) an oligonucleotide primer complementary to a region of at least 10 consecutive nucleotides of positions 76 to 110 of SEQ ID NO: 16, and an oligonucleotide primer complementary to a region of at least 10 consecutive nucleotides of positions 154 to 180 of SEQ ID NO: 16, and
  (b) an oligonucleotide primer complementary to a region of at least 10 consecutive nucleotides of positions 119 to 149 of SEQ ID NO: 16, and an oligonucleotide primer complementary to a region of at least 10 consecutive nucleotides of positions 225 to 246 of SEQ ID NO: 16.

20. The method according to claim 17, wherein said oligonucleotide primers are oligonucleotide primers of group (a), group (b) or group (c):
  (a) an oligonucleotide primer of SEQ ID NO: 1 and/or 2, and one or more oligonucleotide primers selected from the group consisting of SEQ ID NOs: 5, 6, 7 and 8;
  (b) an oligonucleotide primer of SEQ ID NO: 3 and/or 4, and the oligonucleotide primer of SEQ ID NO: 9; and
  (c) an oligonucleotide primer of SEQ ID NO: 3 and/or 4, and the oligonucleotide primer of SEQ ID NO: 10.

* * * * *